(12) United States Patent
Staniforth et al.

(10) Patent No.: US 6,941,948 B2
(45) Date of Patent: Sep. 13, 2005

(54) MEDICAMENT STORAGE AND DELIVERY DEVICES

(75) Inventors: John Nicholas Staniforth, Bath (GB); Michael Tobyn, Wiltshire (GB); Nicolas John Bowman, Herts (GB); Matthew Wright, Suffolk (GB); Gary Stephen Howard, Cambridge (GB); David Bradley Brook Simpson, Bath (GB)

(73) Assignee: Vectura Drug Delivery, Wiltshire (GB)

( * ) Notice: Subject to any disclaimer, the term of this patent is extended or adjusted under 35 U.S.C. 154(b) by 0 days.

(21) Appl. No.: 10/383,408

(22) Filed: Mar. 7, 2003

(65) Prior Publication Data

US 2003/0172924 A1 Sep. 18, 2003

Related U.S. Application Data

(60) Provisional application No. 60/366,710, filed on Mar. 22, 2002, and provisional application No. 60/362,307, filed on Mar. 7, 2002.

(51) Int. Cl.[7] .................. A61M 15/00; A61M 16/00
(52) U.S. Cl. ..................... 128/203.21; 128/203.12; 128/203.15
(58) Field of Search ............... 128/203.12, 203.15, 128/203.21

(56) References Cited

U.S. PATENT DOCUMENTS

| | | | | |
|---|---|---|---|---|
| 3,410,450 A | * | 11/1968 | Fortenberry | 221/7 |
| 3,482,733 A | * | 12/1969 | Groves | 221/25 |
| 3,887,700 A | | 6/1975 | Boncey et al. | 424/44 |
| 4,090,642 A | * | 5/1978 | Baker | 222/94 |
| 4,590,206 A | | 5/1986 | Forrester et al. | 514/456 |
| 4,733,797 A | * | 3/1988 | Haber | 221/8 |
| 5,207,217 A | | 5/1993 | Cocozza et al. | 128/203.21 |
| 5,263,475 A | | 11/1993 | Altermatt et al. | 128/203.15 |
| 5,497,763 A | * | 3/1996 | Lloyd et al. | 128/200.14 |
| 5,505,196 A | | 4/1996 | Herold et al. | 128/203.15 |
| 5,590,645 A | * | 1/1997 | Davies et al. | 128/203.15 |
| 5,607,697 A | | 3/1997 | Alkire et al. | 424/44 |
| 5,702,362 A | | 12/1997 | Herold et al. | 604/58 |
| 6,425,888 B1 | * | 7/2002 | Embleton et al. | 604/290 |
| 2001/0020147 A1 | | 9/2001 | Staniforth et al. | |
| 2003/0175355 A1 | | 9/2003 | Tobyn et al. | |

FOREIGN PATENT DOCUMENTS

| | | | | |
|---|---|---|---|---|
| EP | 0966952 | 12/1999 | | A61K/7/16 |
| EP | 0727146 | 8/2000 | | A23G/1/00 |
| EP | 1219291 | 7/2002 | | A61K/9/00 |
| GB | 2165159 | 4/1986 | | A61M/15/00 |
| WO | 9209322 | 6/1992 | | A61M/15/00 |
| WO | 9325198 | 12/1993 | | A61K/9/72 |
| WO | 9404133 | 3/1994 | | A61K/9/00 |
| WO | 9534337 | 12/1995 | | B01J/20/26 |
| WO | 9623485 | 8/1996 | | A61K/9/00 |
| WO | 9848875 | 11/1998 | | A61M/15/00 |
| WO | 0064520 | 11/2000 | | A61M/15/00 |
| WO | 01064182 | 9/2001 | | A61K/11/00 |
| WO | 03020241 | 3/2003 | | A61K/9/12 |
| WO | 03074029 | 9/2003 | | A61K/9/14 |

OTHER PUBLICATIONS

International Search Report for related PCT Application No. PCT/GB03/00969.

* cited by examiner

*Primary Examiner*—Glenn K. Dawson
*Assistant Examiner*—Michael G. Mendoza
(74) *Attorney, Agent, or Firm*—Davidson, Davidson & Kappel, LLC

(57) ABSTRACT

A multiple dose delivery device for delivering a medicament into an oral cavity of a patient is provided. The device includes a sachet pack including a plurality of unit doses of a medicament enclosed between a first strip and a second strip. The device further includes a sachet advance mechanism and a mouthpiece. Upon actuation by a user, the sachet advance mechanism, which is engaged with the sachet pack, separates the first strip from the second strip to release one of the plurality of unit doses from the sachet pack. The mouthpiece includes an opening, and each released unit dose passes through the opening.

26 Claims, 18 Drawing Sheets

MEDICAMENT STORAGE AND DELIVERY DEVICES

This application claims priority from U.S. Provisional Application No. 60/362,307 filed on Mar. 07, 2002 and No. 60/366,710 filed Mar. 22, 2002, the entire disclosures of which are hereby incorporated by reference.

BACKGROUND OF THE INVENTION

The most prominent mode of delivery of therapeutic agents is by the oral route by means of solid dosage forms such as tablets and capsules. Oral administration of solid dosage forms is more convenient and accepted than other modes of administration, e.g. parenteral administration. However, the manufacture, dispensing and administration of solid dosage forms are not without associated problems and drawbacks.

With the manufacture of solid dosage forms, in addition to the active agent, it is necessary to combine other ingredients in the formulations for various reasons, such as to enhance physical appearance, to provide necessary bulk for tableting or capsuling, to improve stability, to improve compressibility or to aid in disintegration after administration. However, these added excipients have been shown to adversely influence the release, stability and bioavailability of the active ingredient. The added excipients are a particular problem with drugs that require a high dose in order to provide a therapeutic effect, e.g., biphosphonate drugs. The inclusion of the additional excipient can make the final tablet extremely large, which could result in esophogeal damage if the dosage form is not swallowed properly. Further, the tableting of certain drugs has many associated production problems. In particular, many drugs, e.g., acetaminophen, have poor compressibility and cannot be directly compressible into solid dosage forms. Consequently, such drugs must either be wet granulated or manufactured in a special grade in order to be tableted which increases manufacturing steps and production costs.

The adherence to good manufacturing practices and process controls is essential in order to minimize dosage form to dosage form and batch-to-batch variations of the final product. Even strict adherence to these practices still is not a guarantee that acceptable variation will occur.

With the high cost of industrial scale production and governmental approval of solid dosage forms, such formulations are often available in a limited number of strengths, which only meet the needs of the largest sectors of the population. Unfortunately, this practice leaves many patients without acceptable means of treatment and physicians in a quandary, with respect to individualizing dosages to meet the clinical needs of their patients.

The dispensing of oral solid dosage forms also makes the formulations susceptible to degradation and contamination due to repackaging, improper storage and manual handling.

There are also many patients who are unable or unwilling to take conventional orally administered dosage forms. For some patients, the perception of unacceptable taste or mouth feel of a dose of medicine leads to a gag reflex action that makes swallowing difficult or impossible. Other patients, e.g., pediatric and geriatric patients, find it difficult to ingest typical solid oral dosage forms, e.g., due to tablet size.

Other patients, particularly elderly patients, have conditions such as achlorhydria, which hinders the successful use of oral solid dosage forms. Achlorhydria is a condition wherein there is an abnormal deficiency or absence of free hydrochloric acid in the gastric secretions of the stomach. This condition hinders the disintegration and/or dissolution of oral solid dosage forms, particularly dosage forms with high or insoluble excipient payloads Flavored solutions/suspensions of some therapeutic agents have been developed to facilitate the oral administration of oral agents to patients normally having difficulty ingesting conventional solid oral dosage forms. While liquid formulations are more easily administered to the problem patient, liquid/suspension formulations are not without their own significant problems and restrictions. The liquid dose amount is not as easily controlled compared with tablet and capsule forms and many therapeutic agents are not sufficiently stable in solution/suspension form. Indeed, most suspension type formulations are typically reconstituted by the pharmacist and then have a limited shelf life even under refrigerated conditions. Another problem with liquid formulations, which is not as much a factor with tablets and capsules, is the taste of the active agent. The taste of some therapeutic agents is so unacceptable that liquid formulations are not a viable option. Further, solution/suspension type formulations are typically not acceptable where the active agent must be provided with a protective coating, e.g. a taste masking coating or an enteric coating to protect the active agent from the strongly acidic conditions of the stomach.

Another alternative to oral dosage forms for certain medications is aerosol dosage forms, which administer therapeutic agents for deposition to the pulmonary system. The use of aerosol dosage forms has many advantages for the patient. The packaging of the active agent is convenient and easy to use, generally with limited manual manipulation. As the medicine is sealed within the device, direct handling of the medication is eliminated and the contamination of the contents from air and moisture can be kept to a minimum. Further, a metering valve can be included in the device in order to individualize the dose for particular patients. However, such formulations also have drawbacks such as decreased bioavailability of the drug due to improper administration by the patient. For example, if a patient's breathing is not coordinated with the activation of the device, the active agent will not reach its intended site of action which will lead to a decrease in therapeutic benefit.

Another alternative is dry powder dosage forms. For example, International Patent Application WO 94/04133, hereby incorporated by reference, describes a powder composition for inhalation, which contains a microfine drug such as salbutamol sulfate and a carrier containing an anti-static agent. The carrier is calcium carbonate or a sugar, especially lactose. The amount of carrier is 95–99.99 weight percent. The compositions are said to be useful for delivery of the active agent to the lungs while providing reduced side effects such as nausea by maximizing its proportion of drug reaching the lungs.

U.S. Pat. No. 4,590,206, hereby incorporated by reference, describes capsules, cartridges or aerosol containers containing spray-dried sodium cromoglycate in finely divided and un-agglomerated form. A substantial proportion of the individual drug particles have sizes and shapes, which allow deep penetration into the lung and yet are free-flowing so as to allow capsule filling.

International Patent Application WO 93/25198, hereby incorporated by reference, is directed to an ultrafine powder for inhalation. The powder comprises a drug and hydroxypropyl cellulose and/or hydroxypropylmethylcellulose. More than 80 weight percent of the particles in the powder are said to have a particle diameter of 0.5–10 microns. The powder is said to be able to reach the lower windpipe and bronchi.

Due to the disadvantages of known drug delivery discussed above (as well as other disadvantages) there exists a need in the art for the development of a device and method for facilitating delivery of a wide range of therapeutic agents for gastrointestinal deposition and which minimize pulmonary deposition of materials having undesirable or unknown pulmonary toxicology but which are approved for oral delivery.

Oral drug delivery systems, devices and methods for oral powders are disclosed in PCT/IB01/00251, hereby incorporated by reference in its entirety for all purposes.

SUMMARY OF THE INVENTION

In accordance with a first embodiment of the present invention, a multiple dose delivery device for delivering a medicament into an oral cavity of a patient is provided. The device includes a sachet pack including a plurality of unit doses of a medicament enclosed between a first strip and a second strip. The device further includes a sachet advance mechanism and a mouthpiece. Upon actuation by a user, the sachet advance mechanism, which is engaged with the sachet pack, separates the first strip from the second strip to release one of the plurality of the unit doses from the sachet pack. The mouthpiece includes an opening, and each released unit dose passes through the opening. The sachet advance mechanism may be constructed in a variety of ways. For example, the sachet advance mechanism may be constructed using known techniques using gears, cams, levers, linkages, pulleys, pistons, augers, slides, torsion elements, and the like.

In accordance with a second embodiment of the present invention, a delivery device is provided which includes a sachet pack including a plurality of unit doses of a medicament enclosed between a first strip and a second strip. The device includes a first member, a second member, an actuator, and a mouthpiece. The actuator pulls the first strip against the first member and the second strip against the second member to release a unit dose of the medicament from the sachet pack. The mouthpiece is positioned relative to the sachet pack, the first member, and the second member, to deliver the unit dose of the medicament to an oral cavity of a patient.

In accordance with a third embodiment of the present invention, a delivery device is provided which includes a sachet pack including a plurality of unit doses of a medicament enclosed between a first strip and a second strip. The device further includes a first roller, a second roller, an actuator, and a mouthpiece. The first roller is spaced apart forward from the second roller, the first strip is wrapped around the first roller, and the second strip is wrapped around the second roller. The actuator, upon actuation by a patient, pulls the first strip around the first roller and pulls the second strip around the second roller to release a unit dose of the medicament from the sachet pack. The mouthpiece is positioned relative to the sachet pack, the first roller, and the second roller, to deliver the unit dose of the medicament to an oral cavity of the patient.

In accordance with a fourth embodiment of the present invention, a delivery device is provided which includes a sachet pack including a plurality of unit doses of a medicament enclosed between a first strip and a second strip. The device further includes a first roller, a second roller, an actuator, and a mouthpiece. The first roller is spaced apart forward from a second roller, the first strip is wrapped around the first roller, and the second strip is wrapped around the second roller. Upon actuation by a patient, the actuator causes a predetermined rotation of the first and second rollers, the predetermined rotation being selected such that repeated actuation of the actuator will cause successive ones of the plurality of the unit doses to be released from the sachet pack. The mouthpiece is positioned relative to the sachet pack, the first roller, and the second roller, to deliver the unit dose of the medicament to an oral cavity of the patient.

In accordance with a fifth embodiment of the present invention, a delivery device is provided which includes a sachet pack including a plurality of unit doses of a medicament enclosed between a first strip and a second strip. The device further includes a first roller, a second roller, an actuator, and a mouthpiece. The first roller is spaced apart forward from and above the second roller, the first strip is wrapped around the first roller, and the second strip is wrapped around the second roller. Upon actuation by a patient, the actuator pulls the first strip around the first roller and pulls the second strip around the second roller to release a unit dose of the medicament from the sachet pack. The mouthpiece surrounds the first and second rollers and has a top surface, a bottom surface, and a pair of lateral surfaces. The bottom surface has an opening formed therein, and the released medicament passes through the opening.

In accordance with further aspects of the present invention, the mouthpiece of the fifth embodiment may be utilized in the first, second, third, or fourth embodiments. Preferably, the opening of the mouthpiece has a forward edge, a rear edge, and a pair of lateral edges, and the forward edge contacts the first strip and the rear edge contacts the second strip. Most preferably, the first strip separates from the second strip at a separation point, and the separation point is midway between the forward and rear edges.

In accordance with other aspects of the present invention, the actuator of the second, third, fourth, and fifth embodiments may include an actuator input, a drive, a first pair of index rollers, and a second pair of index rollers. This actuator may also form a part of the sachet advance mechanism of the first embodiment. The first pair of index rollers define a first nip therebetween, and the first strip passes through the first nip. The second pair of index rollers defines a second nip therebetween, and the second strip passes though the second nip. The drive is coupled to the actuator input, the first pair of index rollers and the second pair of index rollers. Upon actuation of the actuator input by a patient, the drive causes rotation of the first and second pairs of index rollers, which in turn, pull the a portion of the first and second strips through the first and second nips, respectively. In certain preferred embodiments, the drive may comprise a gear which engages one of the first pair of index rollers and one of the second pair of index rollers, and which gear is coupled to the actuator input such that actuation of the actuator input causes a predetermined rotation of the gear.

In accordance with still other aspects of the present invention, the actuator of the second, third, fourth, and fifth embodiments may include an actuator input coupled to a carriage, and the carriage is coupled to the first and second strips. This actuator may also form a part of the sachet advance mechanism of the first embodiment. With this actuator, actuation of the actuator input causes a movement of the carriage away from the first and second members (in the case of the second embodiment) or from the first and second rollers (in the case of the third fourth and fifth embodiments). Preferably, actuation of the actuator input causes a movement of the carriage from an first position to a second position and then to the first position, the first position being closer to the first and second members than the second position (in the case of the second embodiment) and closer to the first and second rollers than the second position (in the case of the third fourth and fifth embodiments). Most preferably, the carriage may include a first draw roller and a second draw roller. The first and second draw rollers are rotationally fixed when the carriage moves from the first position to the second position. However, the first draw roller rotates to wrap the first strip thereabout when the carriage moves from the second position to the first position, and the second draw roller rotates to wrap the second strip thereabout when the carriage moves from the second position to the first position.

In accordance with other aspects of the present invention, the actuator of the second, third, fourth, and fifth embodiments may include a stored energy component, a stored energy initiator, an actuation trigger, and a draw component. The stored energy component may also form part of,the sachet advance mechanism of the first embodiment. The stored energy initiator is coupled to the stored energy component, and when actuated, stores energy in the stored energy component. In contrast, the actuation trigger, when actuated, releases the energy from the stored energy component. The draw component is coupled to the stored energy component and the draw component pulls the first strip against the first member and the second strip against the second member when the energy is released from the stored energy component. The draw component can be implemented in a variety of ways. For example, the draw component may be comprised of the drive and first and second pairs of index rollers described above, or of the carriage and first and second draw rollers as described above. Most preferably, the stored energy component includes a gear and a torsion element, and the gear of the stored energy component is engaged with the gear of the drive (described above). The torsion element, which may, for example, be a torsion spring, is coupled between the stored energy initiator and the gear of the stored energy initiator.

Preferably, the medicament contained in the sachet packs described above comprise drug particles greater than 10 microns in order to minimize the inhalation of the drug particles into the lungs, in order to have substantially all of the dose deposited in the gastrointestinal system. The mean drug particle size of the unit dose is greater than 10 $\mu$m and preferably greater than about 50 $\mu$m in order to minimize pulmonary aspiration of the drug such that an effective dose of said drug cannot be delivered into the lower lung of a human patient. However, the medicament may alternately be in the form of a semi solid or a liquid.

The term "drug" or "medicament" refers to any agent which is capable of providing a therapeutic effect to a patient upon gastrointestinal deposition. This encompasses all drugs which are intended for absorption for a systemic effect (regardless of their actual bioavailability) as well as drugs intended for a local effect in the gut and/or oral cavity, e.g. nystatin, antibiotics or local anesthetics.

The term "particle size" refers to the diameter of the particle.

The term "deposition" means the deposit of the unit dose at the intended point of absorption and/or action. For example, gastrointestinal deposition means the intended deposit of the unit dose in the gastrointestinal system for e.g., absorption for a systemic effect or to exert a local effect. Pulmonary deposition means the intended deposit of drug into the lungs in order to provide a pharmaceutical effect, regardless that the unit dose may enter the oral cavity prior to pulmonary deposition.

The term "dispense", when used in connection with the devices and systems of the present invention, means that the device or system delivers the unit dose ex vivo with the intent of subsequent administration to a mammal. For example, the device or system can dispense the unit dose into a food, a liquid, a spoon, or another intermediate receptacle.

The term "administer", when used in connection with the devices and systems of the present invention, means that the device or system delivers the unit dose in vivo, i.e., directly into the gastrointestinal tract of a mammal.

The term "deliver" is meant to cover all ex vivo and in vivo delivery, i.e., dispensing and administering, respectively.

The term "patient" refers to humans as well as other mammals in need of a therapeutic agent, e.g., household pets or livestock. This term also refers to humans or mammals in need of or receiving prophylactic treatment.

In certain embodiments, the particulates are defined functionally with respect to the fact that they are of a size such that an effective dose cannot be delivered into the lower lung of a human patient via the devices described herein. However, this definition should be understood to mean that a small percentage of drug (but not an amount effective to render a therapeutic effect) may in fact be inadvertently delivered to the lungs of the patient. Also, this definition is meant to define the particles, but not to limit the use of the invention to the treatments of humans only. The invention may be used for delivering doses of drugs to other mammals as well.

DETAILED DESCRIPTION OF THE PREFERRED EMBODIMENTS

Drug delivery devices in accordance with the present invention are designed to store multiple doses of a medicament, and to deliver a unit dose of the medicament into the oral cavity of a patient for gastrointestinal (e.g., gastric, intestinal, and/or colonic) absorption or action; esophageal absorption or action; and/or absorption or action in the oral cavity (e.g., sublingual, lingual, or buccal). This is to be distinguished from prior art insufflation delivery devices which are designed to deliver medicament into the lungs (e.g., pulmonary deposition) or into the nasal passages.

Figure 1:
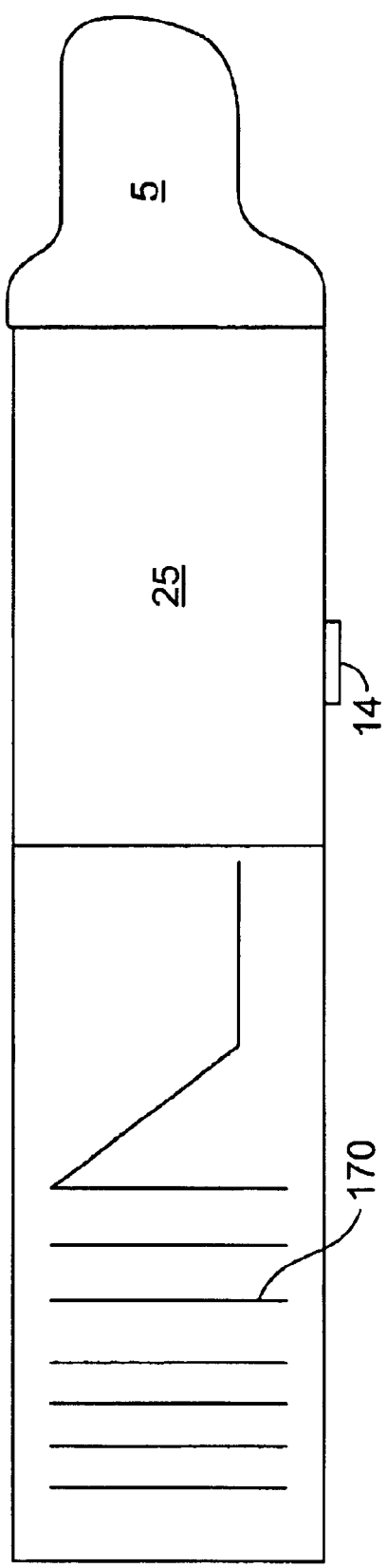
FIG. 1 shows a partial cross-section through a drug delivery device including a sachet advance mechanism.

FIG. 1 shows a partial cross-section through a drug delivery device including a sachet advance mechanism 25 including an actuator input 14, a mouthpiece 5, and a sachet pack 170. The sachet pack 170 includes a plurality of unit doses of a medicament enclosed between a first strip and a second strip. Upon actuation by a user via the actuator input 14, the sachet advance mechanism 25, which is engaged with the sachet pack 170, separates the first strip from the second strip to release one of the plurality of the unit doses from the sachet pack. The mouthpiece 5 includes an opening (not shown), and each released unit dose passes through the opening. The sachet advance mechanism may be constructed in a variety of ways. For example, the sachet advance mechanism may be constructed using known techniques using gears, cams, levers, linkages, pulleys, pistons, augers, slides, torsion elements, and the like. Although the actuator input 14 is shown located on the top of the device, it may alternatively be located on one of the sides to provide a more ergonomic design (e.g., so that the button is located at a convenient location for the user's thumb when in use).

Figure 2:
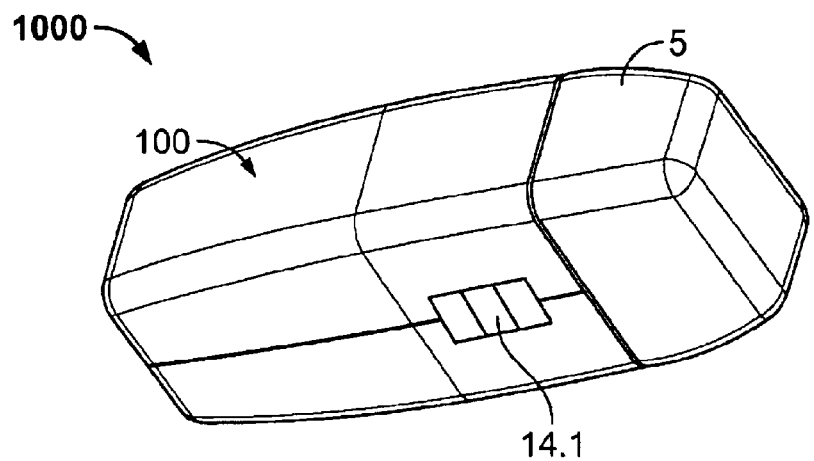
FIG. 2 shows a perspective view of a drug delivery device in accordance with an embodiment of the present invention.
Figure 3:
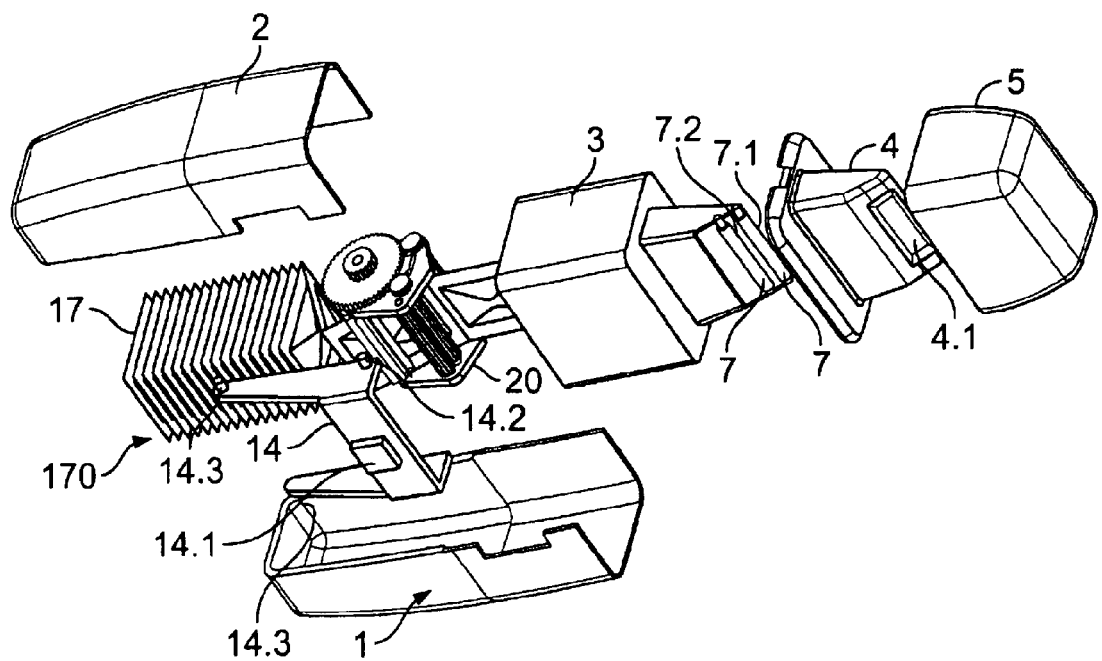
FIG. 3 is an exploded perspective view of the drug delivery device of FIG. 2.

FIG. 2 shows a perspective view of a drug delivery device 1000 in accordance with a first embodiment of the present invention, and FIG. 3 shows an exploded perspective view of FIG. 2. Further details of the device 1000 are shown in FIGS. 4(a,b). Referring to FIG. 3, a drug delivery device 1000 includes a housing 100 comprised of a first body portion 1 and a second body portion 2. The sachet pack 170 described above is shown in further detail in FIG. 4(b). The sachet pack 170 is comprised of a plurality of individual sachets 17, and is stored within the housing 100. The sachet pack 170 is a continuous sheet which is comprised of a pair of strips 1701, 1702 which are adhered to each other and which enclose a medicament.

The device 1000 includes a chassis 3 having a pair of lead rollers 7.1, 7.2 (collectively, lead rollers 7), wherein roller 7.1 is offset forward and above with respect to roller 7.2 as shown in FIG. 3. A sachet drive mechanism 20, which is partially enclosed within a hollow interior of chassis 3, is operable to sequentially feed each sachet 17 from sachet pack 170 through lead rollers 7. Sachet drive mechanism 20 is driven by actuator 14. Chassis 3, sachet drive mechanism 20, sachet pack 170, and actuator 14 are enclosed within the housing 100 as shown in FIGS. 2 and 3. However, a portion of actuator 14 (e.g., button 14.1) is accessible through an opening in the housing 100 in order to allow a patient to operate the actuator 14. In this regard, button 14.1 may be flush with the outer surface of housing 100, may be recessed with respect to the outer surface of the housing 100, or may extend beyond the outer surface of the housing 100.

A mouthpiece 4 is secured to the housing 100. As a sachet passes through rollers 7.1, 7.2 under the control of the sachet drive mechanism 20, the opposing adhered strips 1701, 1702 separate, releasing the medicament. The mouthpiece 4 includes an opening 4.1 for delivering the medicament. A cover 5 is removably secured to the mouthpiece 4 and/or housing 100 via, for example, a friction fit. FIG. 3 shows a perspective view of the device 1000, with the cover 5 secured to the mouthpiece 4/housing 100.

Figure 4A:
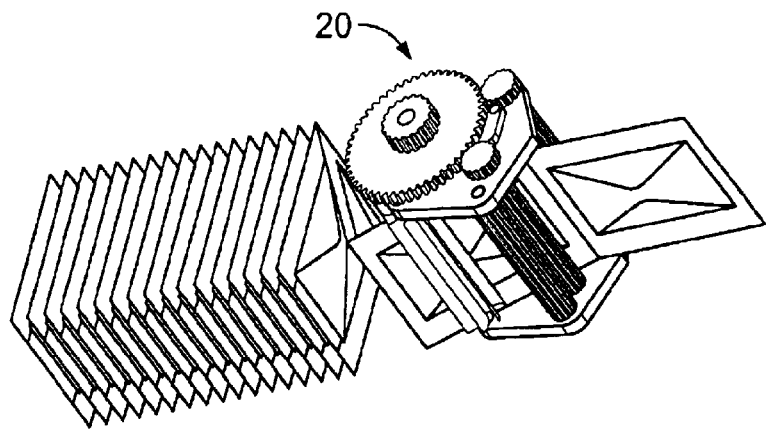
FIG. 4(a) is a perspective view of the sachet drive assembly of the drug delivery device of FIG. 1.
Figure 4B:
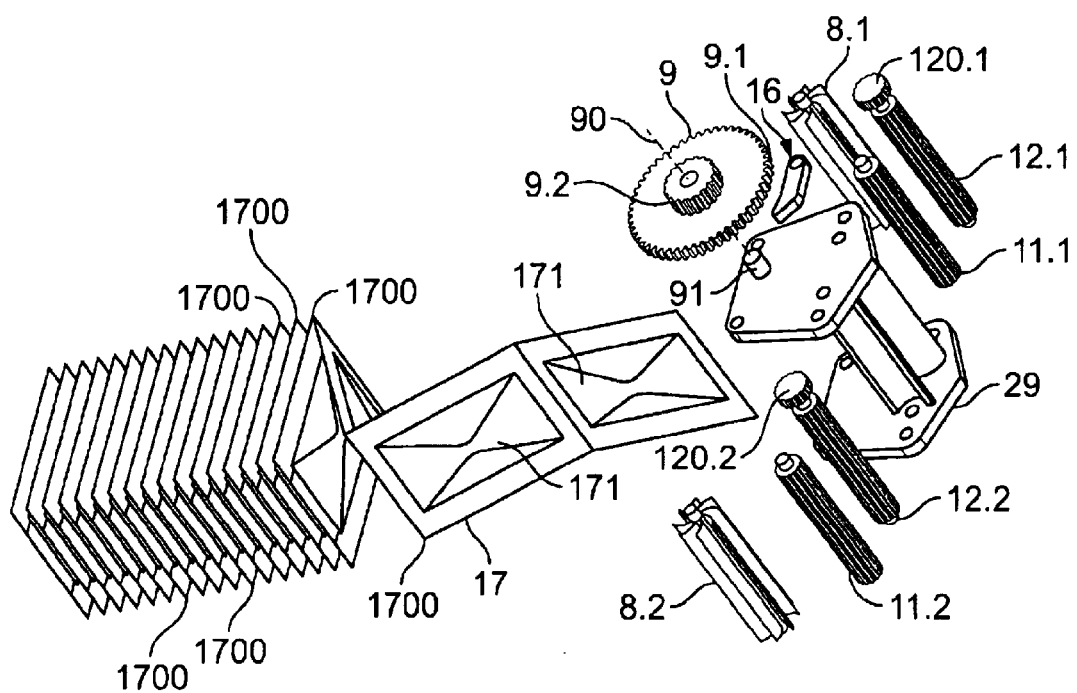
FIG. 4(b) is an exploded perspective view of one embodiment of the sachet drive mechanism.
Figure 5:
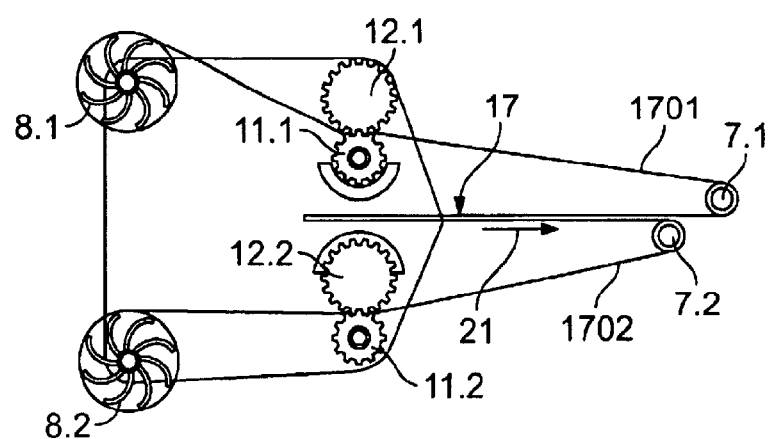
FIG. 5 is a simplified view of the lead rollers of the chassis and the various gears and rollers of the sachet drive mechanism of FIGS. 4(a, b).

FIG. 4(a) shows a perspective view of the sachet drive mechanism 20, and FIG. 4(b) is an exploded view of FIG. 4(a). FIG. 5, in turn, illustrates the interaction between drive mechanism 20 and rollers 7. Using the coordinates (left, right, upper, lower) shown in FIGS. 4 and 5 for purposes of illustration, upper and lower index rollers 12.1 and 11.1 are rotatably secured to an upper right portion of the chassis of mechanism 20, upper and lower index rollers 12.2 and 11.2 are rotatably secured to a lower right portion of chassis 29, a waste roller 8.1 is rotatably secured to an upper left portion of chassis 29, and a waste roller 8.2 is rotatably secured to a lower left portion of chassis 29.

Referring to FIG. 4(a,b)(collectively, "FIG. 4"), sachet pack 170 is comprises a continuous sheet which includes a plurality of individual sachets 17. Preferably, the sachet pack 170 includes at least two, and up to 90, or more individual sachets 17. Each individual sachet 17, in turn, may contain, for example, between about 50 mg and 1 g of a powder/particulate medicament or about 0.5 ml to about 5 ml of a liquid or semi-solid medicament. In the embodiment shown in FIG. 4, each individual sachet 17 is separated by each adjacent sachet by a fold 1700 so that the sachets 17 can be folded one on top of the other as illustrated in FIGS. 3 and 4. In certain embodiments, the folds 1700 maybe perforated.

As noted above, the continuous sheet which comprises the sachet pack is, in fact, itself comprised of a pair of opposing strips 1701, 1702 which are adhered to each other and which enclose a medicament. As shown in FIG. 4, in the preferred embodiment, the medicament is not distributed throughout the continuous sheet. Rather, the medicament is isolated in medicament containing regions 171 on each individual sachet. Preferably, only one medicament containing region 171 is provided on each individual sachet, and each medicament containing region 171 includes a unit dose of medicament.

Referring to FIG. 5, the continuous sachet sheet is fed in a direction 21 towards rollers 7 in chassis 3. After the continuous sheet passes through roller 7.2, strip 1702 is wrapped around roller 7.2 and is fed into a nip formed between rollers 12.2 and 11.2, and strip 1701 is wrapped around roller 7.1 and is fed into a nip formed between rollers 12.1 and 11.1. After exiting the nip formed between rollers 12.1, 11.1, strip 1701 is wrapped around waste roller 8.1, and after exiting the nip formed between rollers 12.2, 11.2, strip 1702 is wrapped around waste roller 8.2. Preferably, roller 8.1 and 8.2 are biased in a counterclockwise direction so that strips 1701, 1702 are wound around respective rollers 8.1, 8.2 as they exit from the aforementioned nips.

Referring to FIG. 4, rollers 12.1 and 12.2 include driven gears 120.1 and 120.2 which, in turn, are engaged with outer teeth 9.1 of drive gear 9. Drive gear 9 is rotatably secured to axle 91 for rotation about axis 90. A gear lock 16 pivotably secured to carriage 29 and is biased (e.g., via a spring) for movement in clockwise direction. Gear lock 16 is engaged with gear 9 to prevent gear 9 from rotating in a counterclockwise direction. In certain embodiments, waste rollers 8.1, 8.2 may be driven by gear 9, rather than being biased (e.g., via a spring). In other embodiments, the waste rollers 8.1, 8.2 may be omitted entirely.

Referring again to FIG. 3, actuator 14 is shown as a lever pivotably secured to housing 100 via axes 14.3. When button 14.1 on actuator is pressed inward towards the device 1000, protrusion 14.2 engages the inner teeth 9.2 of gear 9, causing gear 9 to rotate in a clockwise direction. One full stroke of the actuator 14 rotates the gear 9 by a fixed amount. The gear ratios between the gears 9, 11.1, and 11.2 are selected such that one individual sachet 17 is opened each time the actuator 14 is pressed. Although a simple gear arrangement is shown, it should be appreciated that additional or alternative elements, such as gears, linkages, belts, chains, pulleys, sprockets, and the like may be incorporated into the design in order to adjust the force that needs to be applied to the actuator button 14.1 by the patient in order to cause a full stroke of the actuator.

In FIGS. 2–5, rollers 11.1. 11.2, 12.1, and 12.2 are illustrated as extended gears in order to provide a particularly firm grip on the sachets 17. It should be appreciated, however, that other roller profiles can alternatively be used. For example, by applying an appropriate nip pressure, a roller with a smooth profile can be used.

Preferably, the device 1000 is a disposable delivery device which is sold with the sachet pack 170 loaded and ready for use. When the device 1000 is assembled, strips 1701 and 1702 are wrapped around rollers 7.1, 7.2, passed through rollers 11.1, 12.1, 11.2, 12.2, with the end of strip 1701 secured to waste roller 8.1 and the end of strip 1702 secured to waste roller 8.2, and with an individual sachet 17 positioned relative to the rollers 7.1, 7.2 such that actuation of the actuator 14 will cause the medicament contained in the individual sachet 17 to be dispensed. Preferably, the sachet pack 170 is manufactured with a lead section which does not include any medicament containing regions 171, but rather, is intended to facilitate loading of the sachet pack into the device.

A second embodiment of the present invention (device 1000') is illustrated in FIGS. 6–10, with similar components bearing similar reference numerals to FIGS. 1–5.

Figure 6:
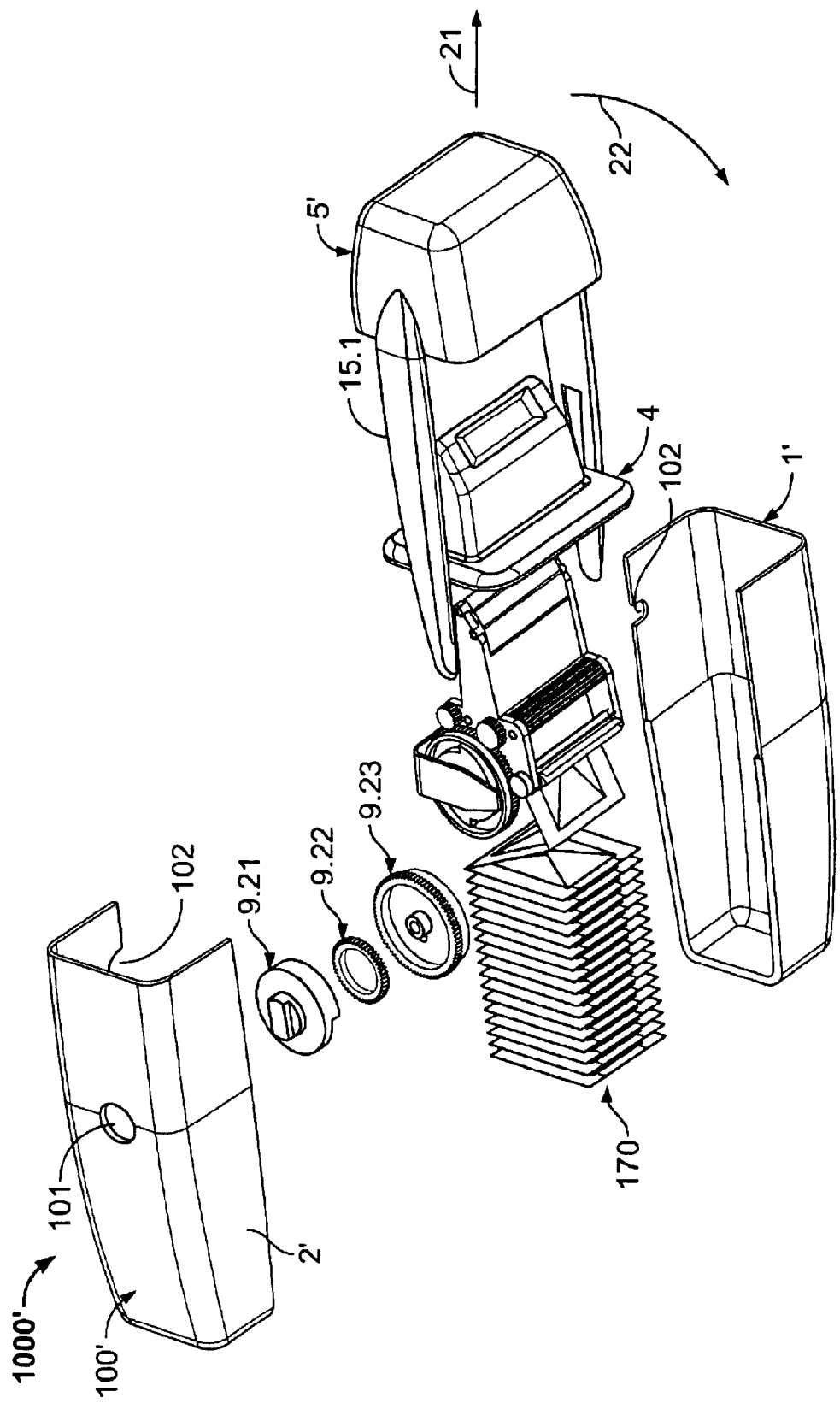
FIG. 6 is an exploded perspective view of a drug delivery device in accordance with another embodiment of the present invention, including a stored energy component.
Figure 7:
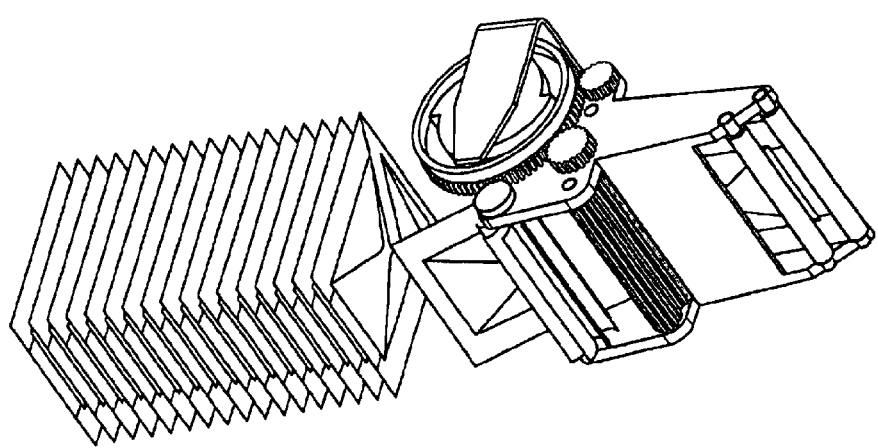
FIG. 7 is a perspective view of the chassis of the drug delivery device of FIG. 6.
Figure 8:
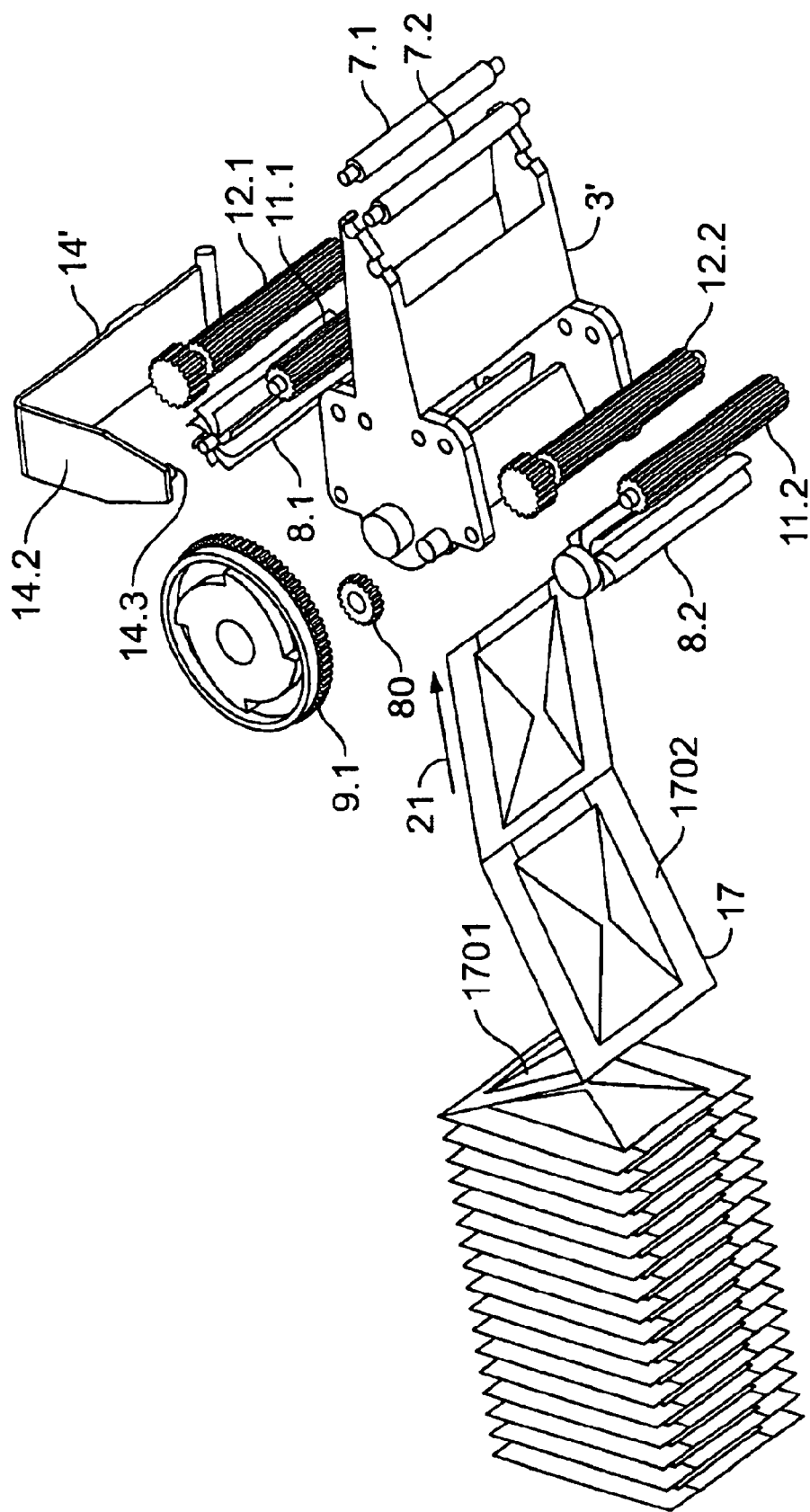
FIG. 8 is an exploded perspective view of the chassis of FIG. 7.
Figure 10A:
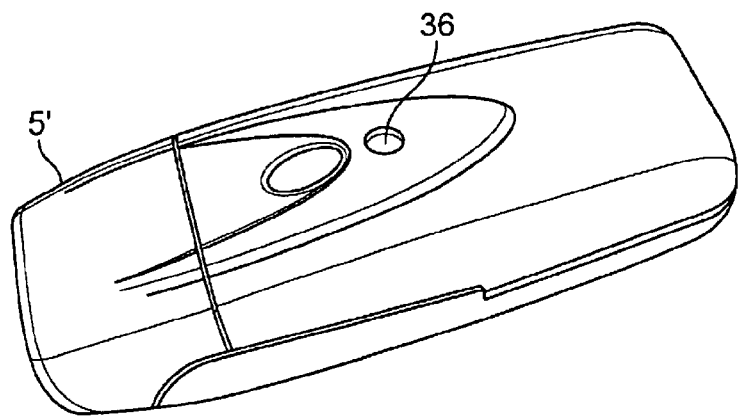
FIG. 10(a) is a perspective view of the drug delivery device of FIG. 6 in a closed position.
Figure 10B:
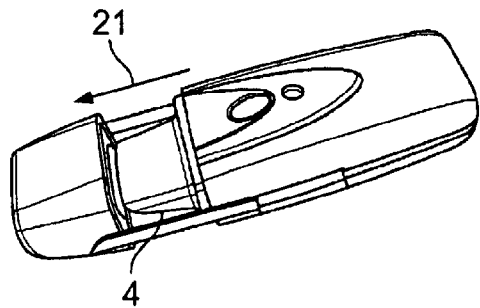
FIG. 10(b) and 10(c) are perspective views of the drug delivery device of FIG. 6 as it is being opened and prepared for use by a patient.
Figure 10C:
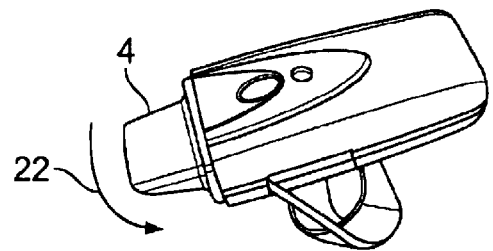
Figure 10D:
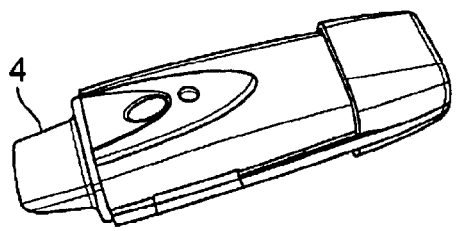
FIG. 10(d) is a perspective view of the drug delivery device of FIG. 6 when it is open and ready for use by a patient.
Figure 11A:
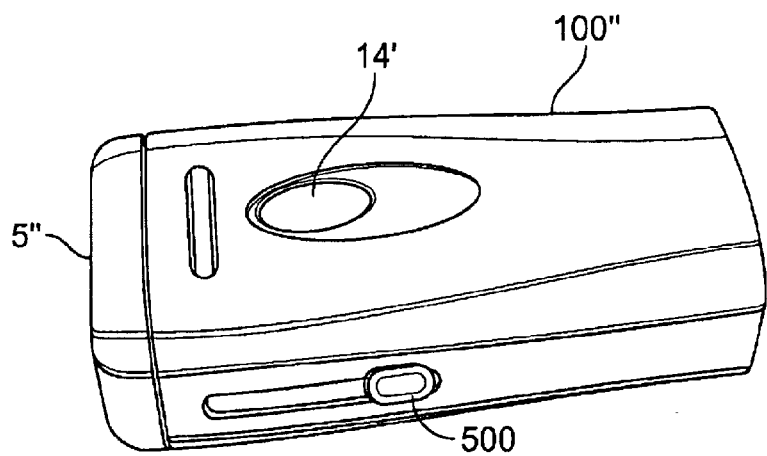
FIG. 11(a) is a perspective view of a drug delivery device according to another embodiment of the present invention in a closed position.
Figure 11B:
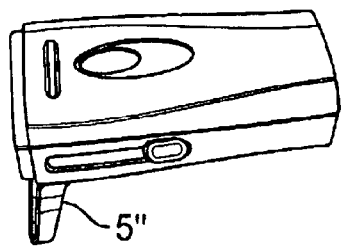
FIG. 11(b) is a perspective view of the drug delivery device of FIG. 11(a) with its cover open.
Figure 11C:
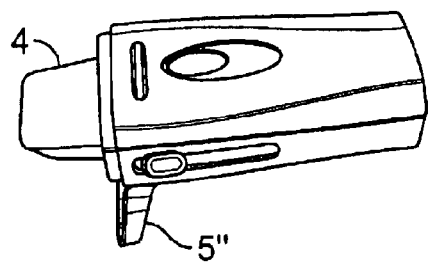
FIG. 11(c) is a perspective view of the drug delivery device of FIG. 11(b) when it is ready for use by a patient.
Figure 11D:
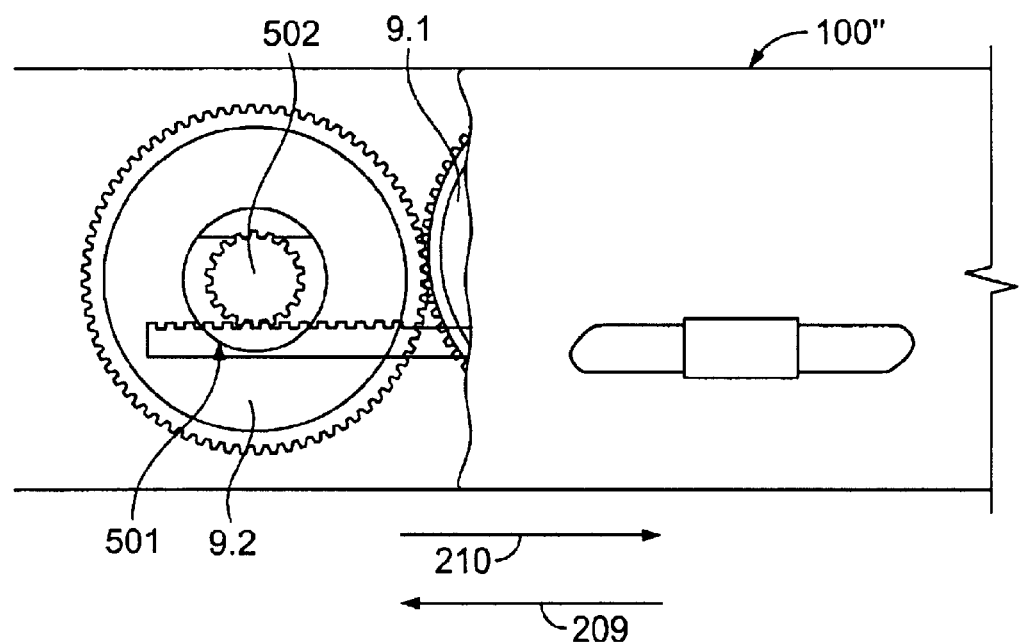
FIG. 11(d) is a partial cross-section through a side of the device of FIG. 11(a), showing a stored energy component.
Figure 11E:
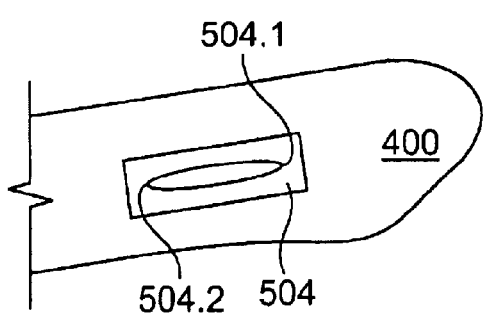
FIG. 11(e) shows a side view of a moveable component of FIG. 11(a).
Figure 11F:
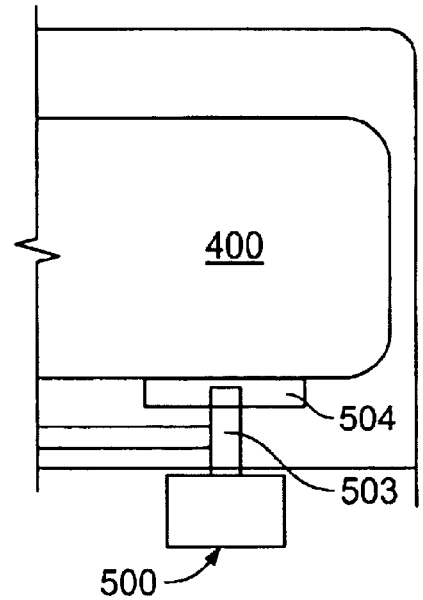
FIG. 11(f) shows a top view of the moveable component engaged with an exemplary stored energy initiator.

Referring to FIGS. 10(a)–10(d), in use, a patient moves cover 5' first in a direction 21 (FIGS. 6 and 10(b)), and then in a direction 22 (FIGS. 6 and 10(c)) to expose the mouthpiece 4. Preferably, the cover 5' can be secured on the rear of the housing 100' as shown in FIG. 10(d). As the cover 5' moves in the direction 22 (clockwise from the perspective in FIG. 6 and counterclockwise from the perspective in FIG. 10(b)), lever 5.1 turns cover hinge 9.21 clockwise (from the perspective of FIG. 6), thereby tensioning torsion spring 9.22, which, in turn, applies a clockwise force to gear 9.23.

Figure 9:
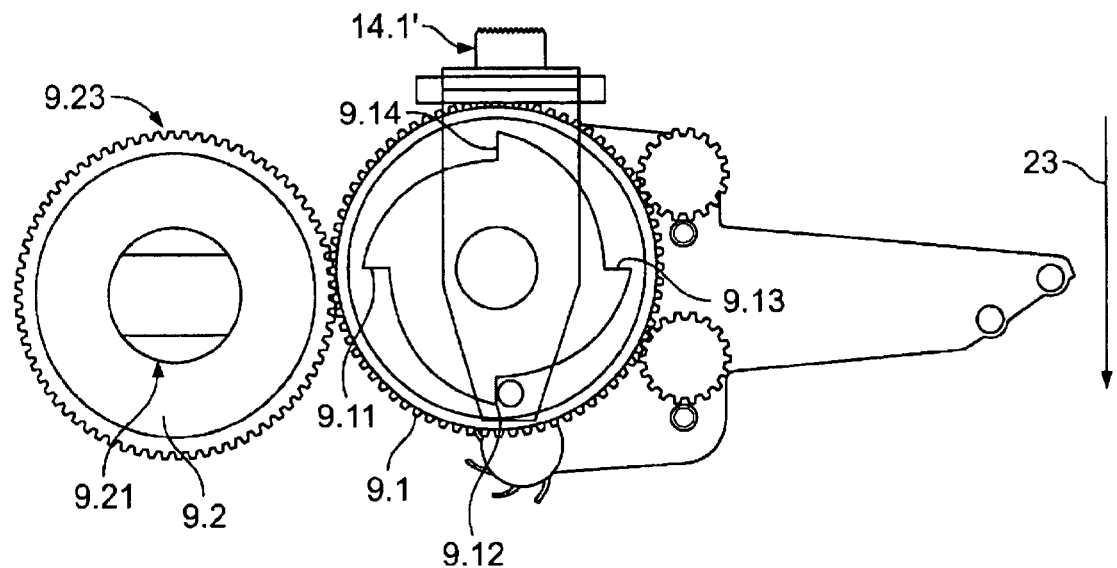
FIG. 9 is a simplified side view of the chassis of FIG. 7, including a stored energy component.

As shown in FIGS. 6 and 9, actuator 14' includes an index button 14.1' which extends through opening 102 in housing 100'. Actuator 14' further includes an arm 14.2 having a protrusion 14.3. Arm 14.2 extends between gear 9.1 and housing part 2'. Index gear 9.1 includes four stops 9.11 through 9.14. Actuator 14' is biased so that, when no force is applied to button 14.1', the actuator 14' is in the position shown in FIG. 9, with the protrusion 14.3 engaged against one of the four stops 9.11 though 9.14. When button 14.1' is pressed, protrusion 14.3 moves in a direction 23, becomes disengaged from the stop (in this case stop 9.12), and the index gear 9.1 moves counterclockwise 90 degrees under the force of the cover hinge gear 9.2, thereby driving gears 120.1, 120.2, and 80 and releasing the medicament from the next sachet 17 in the sachet pack 170.

Rotation of the gear 9.1 can be controlled to release medicament from only one sachet 17 in a number of ways. For example, the tension in the torsion spring 9.22 and the size of the gear 9.23 relative to gear 9.1 can be selected so that the clockwise force applied to gear 9.23 is sufficient only to rotate gear 9.1 90 degrees. Alternatively, actuator 14' could be configured to allow protrusion 14.3 to move in the direction 23 only momentarily, regardless of whether or not the user continued to press button 14.1'. Preferably, both of these techniques are used.

It should be noted while the use of four stops (9.11 to 9.14) to generate a 90 degree rotation of gear 9.1 is advantageous, it is by no means required. For example, two stops could be used to generate a 180 degree rotation of gear 9.1, six stops could be used to generate a 60 degree rotation, eight stops could be used to generate a 45 degree rotation, and so on. The desired rotation is a function of the size of the sachet 17 and the relative sizes of the various gears 9.1, 120.1, 120.2, and 80.

If the index button 14.1' is not pressed, the tension in the torsion spring 9.22 will be released when the cover 5' is returned to its original position over the mouthpiece as shown in FIG. 10(a).

An alternative embodiment which utilizes a cover hinge gear 9.2 and index gear 9.1 is shown in FIGS. 11(a–f). In accordance with this embodiment, the torsion spring 9.22 is tensioned not by the removal of cover 5', but by moving actuator 500 laterally from the position shown in FIG. 11(b) to the position shown in FIG. 11(c). Moreover, in accordance with the embodiment of FIG. 11(a–c), this lateral movement of actuator 500 also causes mouthpiece 4' to move from its retracted position (as shown in FIGS. 11(a,b)) to its extended position (as shown in FIG. 11(c)).

A simple mechanism for accomplishing this functionality is shown in FIGS. 11(d, e, f), with similar components bearing similar reference numerals to FIG. 9. It should be appreciated, however, than alternative mechanisms may also be used. Referring to FIG. 11(e, f), the chassis 3 (including, e.g, gears 9.1, 12.1, 11.1, 12.2., 11.2 et al), gear 9.2, and mouthpiece 4' together comprise a movable component 400 that is mounted within housing 100 for lateral movement in directions 209 and 210. Actuator 500 is coupled to rack 501, which, in turn, is engaged with gear 502. Gear 502, in turn, is connected to torsion spring.6 so that a counterclockwise movement of gear 502 tensions torsion spring 6, and a clockwise movement of gear 502 releases the tension in torsion spring 6. Therefore, when actuator 500 is moved in direction 210, torsion spring 6 is tensioned, such that actuation of button 14 will cause a next sachet 17 is the sachet pack 170 to be opened as described above with regard to FIG. 9.

Actuator 500 is also engaged with slot 504 on movable component 400. When actuator 500 is in its rearward position (as shown in FIGS. 11(a, b)), its shaft 503 rests against rear end 504.2 of slot 504. As actuator moves in direction 210, torsion spring 6 is tensioned by rack 501 and gear 502 (as described above) until shaft 504 contacts front end 504.1 of slot 504. After shaft 504 contacts front end 504.1, movable component 400 moves in the direction 210 under the direction of actuator 500 and shaft 503, until mouthpiece 4 reaches the extended position shown in FIG. 11(c). At this point, the device is ready for use by the patient.

By moving actuator 500 in the direction 209, any tension in torsion spring 6 is released, and after contacting rear end 504.2, movable component 400 moves in the direction 209 until the mouthpiece 4 reaches the retracted position shown in FIG. 11(a,b).

While the mechanisms discussed above are preferred, it should be appreciated that alternative devices for delivering a medicament from a sachet can alternatively be used. For example, referring to FIGS. 12(a–e), an alternative design is shown, with similar components bearing similar reference numerals to FIGS. 1–9. In this embodiment, an actuator 14" is biased in the position shown in FIG. 12(e), and is movable in a direction 24 to dispense the medicament from a next sachet 17 in a sachet pack. Actuator 14" is coupled to a carriage 3". Carriage 3" includes, as draw rollers, waste rollers 8.1" and 8.2". Waste rollers 8.1" and 8.2" are biased for rotation in a clockwise direction from the perspective of FIG. 12(a). The continuous sachet sheet is fed in a direction 21. Strip 1702 is wrapped around roller 7.2 and is then wrapped around waste roller 8.2 whereas strip 1701 is wrapped around roller 7.1 and is then wrapped around waste roller 8.1.

Figure 12A:
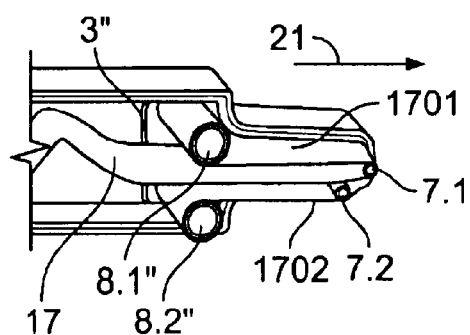
FIGS. 12(a–d) show a cross-section through a side of a drug delivery device according to another embodiment of the present invention.
FIG. 12(e) shows a side view of the drug delivery device of FIG. 12(a–d).
Figure 12B:
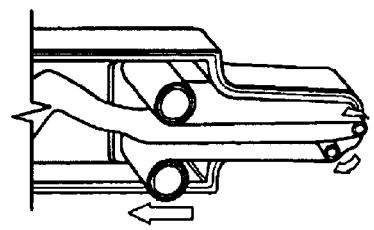
Figure 12C:
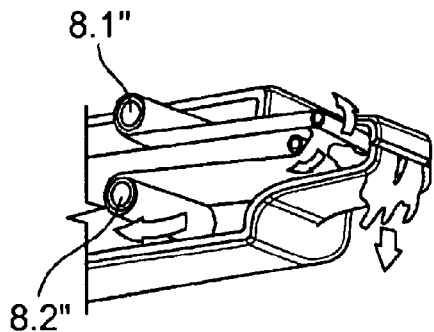
Figure 12D:
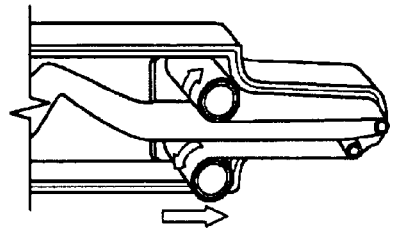
Figure 12E:
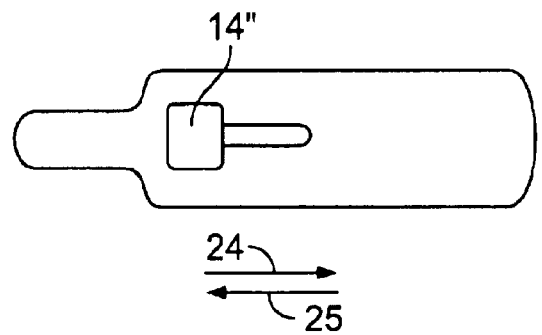

When actuator 14" is in the position shown in FIG. 12(e), carriage 3" is in the position shown in FIG. 12(a). As actuator 14' moves in the direction 24, carriage 3" and waste rollers 8.1" and 8.2" also move in the direction 24, pulling strips 1701 and 1702 around rollers 7.1 and 7.2, respectively, and releasing medicament from the next sachet 17 in the sachet pack as shown in FIG. 12(c). When the actuator 14" is released, it will move in the direction 25, until it returns to its initial position as shown in FIG. 12(d). Since the waste rollers 8.1" and 8.2" are biased for clockwise rotation, they will collect the "spent" portion of strips 1201 and 1202 as they move in the direction 25.

Figure 13:
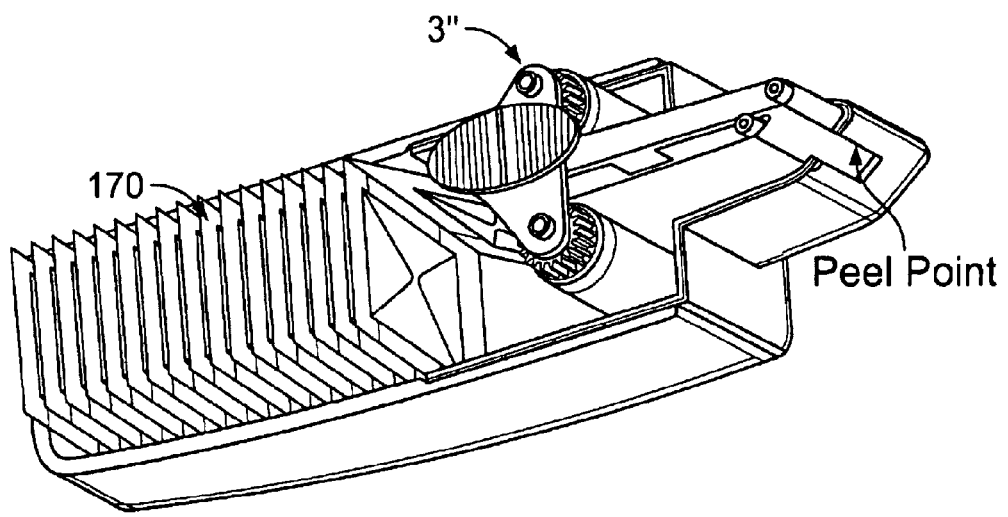
FIG. 13 shows a cross-section through a side of the drug delivery device according to the embodiment of FIG. 12(a–e) with a "scraping" type mouthpiece.
Figure 14:
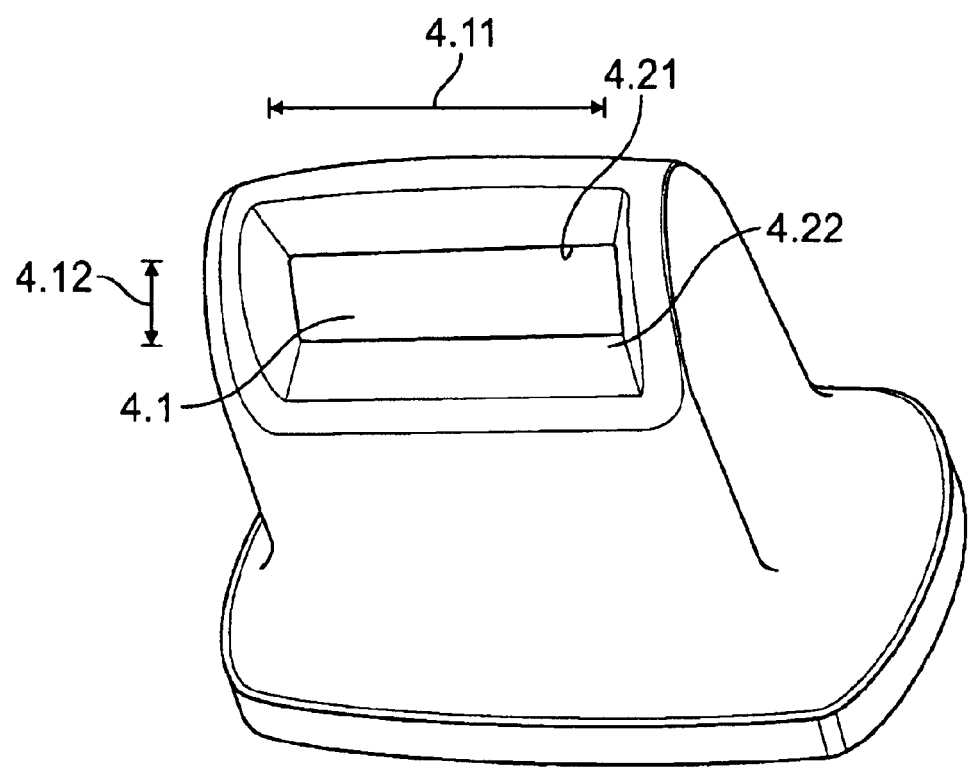
FIG. 14 shows a perspective view of a "scraping" type mouthpiece in accordance with an embodiment of the present invention.
Figure 15A:
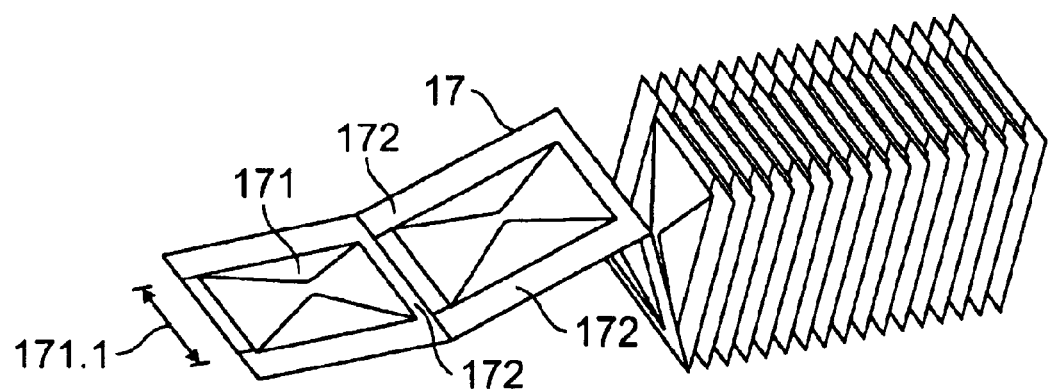
FIG. 15(a) shows a sachet pack in further detail

A wide variety of mouthpiece designs can be used in accordance with the various embodiments of the present invention. Preferably, however, the mouth piece is of the "scraping" type design shown in FIGS. 1–11, and 13. Referring to FIG. 14, the mouthpiece 4 covers the rollers 7, and the opening 4.1 in the mouthpiece has a length 4.11 and a width 4.12. The length 4.11 is at least equal to, and preferably greater than, the width 171.1 (FIG. 15a) of the medicament containing region 171 of the sachet. Moreover, the "peel point" or "separation point" of the sachet (i.e., the point at which the sheet 1701 separates from sheet 1702) is approximately at the midpoint of the width 4.12 of the opening 4.1, as illustrated in FIG. 13. Lengthwise edges 4.21 and 4.22 are in adjacent to strips 1701 and 1702 respectively, to prevent powder that remains on the strips after the sachet has been opened from entering the interior of the device. In this regard, the edges 4.21 and 4.22 are sufficiently close to (and, in some embodiments, in contact with) the strips 1701, 1702 respectively to remove the medicament from the strips as they pass.

When a dose of medicament is administered, a sachet 17 will be advanced and opened via rollers 7, and the majority of the medicament contained in the sachet 17 will be deposited on the tongue of the patient. Some powder, however, may be retained on the edges of the slot 4.1, as the combination of saliva and condensation may cause some adherence of the medicament. This medicament, however, can be removed by the patient using the tongue or lips. Any medicament remaining on the mouthpiece can be clearly seen by the patient, and the mouthpiece can, then be reinserted into the mouth of the patient for removal of the medicament.

As noted above, sachets are widely used in the art as packaging for pharmaceutical products. Two exemplary prior art sachet designs are illustrated in FIG. 15(a,b).

Referring to FIG. 15(a, b), each strip 1701, 1702 in one prior art sachet design is comprised of an exterior paper layer 8000 adhered to an aluminum foil layer 8002 via polythene adhesive 8001. Below the aluminum foil layer 8002 is an ionmer layer 8003 and a wax laquer layer 8004. The wax laquer layer 8004 of strip 1701 faces the wax laquer layer 8004 of strip 1702, and the paper layers 8000 of strips 1701 and 1702 form the exterior surface of the sachet 17. The medicament is isolated in a medicament containing region 171 in each sachet 17, as described above. The sachet 17 is heat sealed by. applying heat and pressure to the non-medicament containing regions 172 of the sachet, causing the wax laquer 8004 (which is a heat sensitive adhesive) of strip 1701 to adhere to the wax laquer 8004 of strip 1702.

Figure 15B:
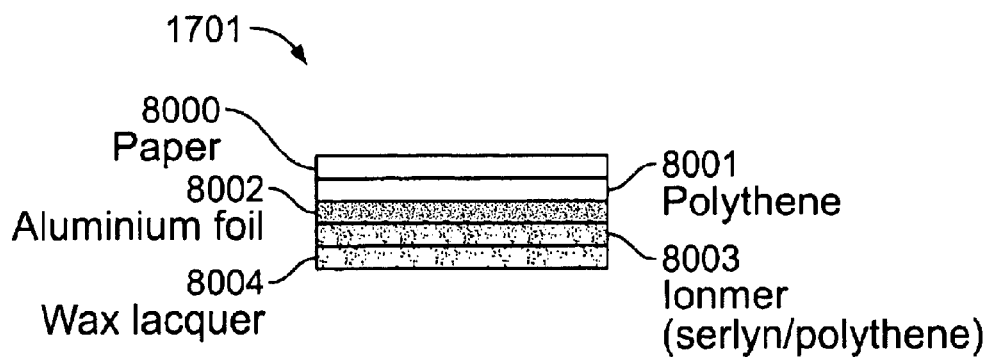
FIGS. 15(b,c) illustrate the composition of two prior art sachet packs that can be used in conjunction with the various embodiments of the present invention.
Figure 15B:
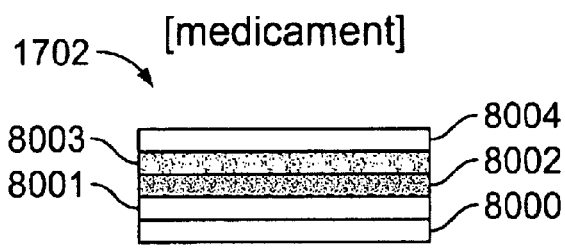
Figure 15C:
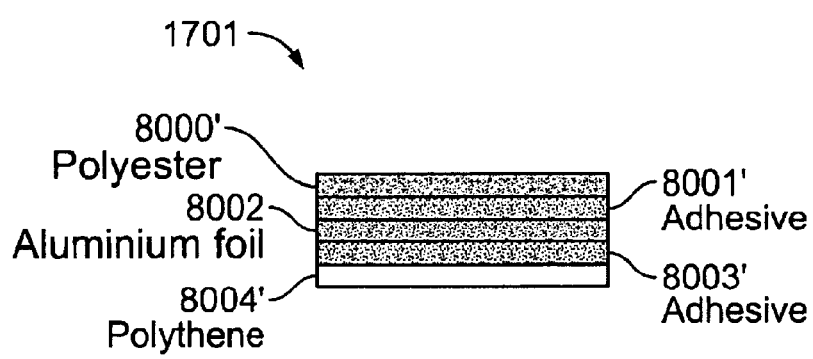
Figure 15C:
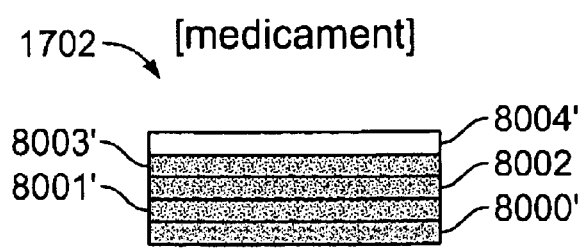

Referring to FIG. 15(c), each strip 1701, 1702 in another prior art sachet design is comprised of an exterior polyester layer 8000' adhered to an aluminum foil layer 8002 via an adhesive 8001'. Below the aluminum foil layer 8002 is an adhesive layer 8003' and a polythene layer 8004'. (Polythene layer 8004' can be polypropylene, polyethyline, etc.) The polythene layer 8004' of strip 1701 faces the polythene layer 8004' of strip 1701, and the polyester layers 8000' of strips 1701 and 1702 form the exterior surface of the sachet 17. The medicament is isolated in a medicament containing region 171 in each sachet 17, as described above. The sachet 17 is heat sealed by applying heat to the non-medicament containing regions 172 of the sachet, causing the polythene 8004' (which is a heat sensitive adhesive) of strip 1701 to adhere to the polythene 8004' of strip 1702.

It should be appreciated that the exemplary sachet designs of FIGS. 15(b) and 15(c) are merely two examples of the many existing sachet designs known in the art, and that any sachet which is capable of being peeled apart in the manner set forth above is suitable for use in conjunction with the present invention. Particularly preferred materials include peelable flexible strips which include aluminum and polypropylene.

Moreover, although the embodiments described above utilize a sachet pack including sachets that are folded over one another prior to use, alternative arrangements may also be employed. For example, the sachet pack could be stored in the device as a roll. In such an embodiment, the individual sachets need not be separated from each other via folds.

Unlike many devices, the delivery devices described herein can be used without regard to the angle of administration. In other words, the dose is effectively delivered out of the device regardless of whether the patient head is bent forward, bent back, or is upright. In many devices, the medicament must be 'metered' accurately from a hopper to the mouthpiece. For this reason, such devices are often sensitive to the angle that the device is held. In other words, with such devices, it may not be possible to consistently deliver an accurate dose, unless the device is held, for example, in an upright position. With the embodiments of the present invention described above, the medicament is released from a sachet at a location sufficiently close to the mouthpiece such that the medicament is delivered out of the mouthpiece via the force of gravity. Moreover, in the preferred embodiments of the present invention, the medicament is released from the sachet while it is directly above the opening in the mouthpiece, thereby ensuring that the medicament will be delivered to the mouth of the patient via the force of gravity (assuming, of course, that the device is positioned so that the opening in the mouthpiece is at angle to horizontal of less than 90 degrees).

Figure 16A:
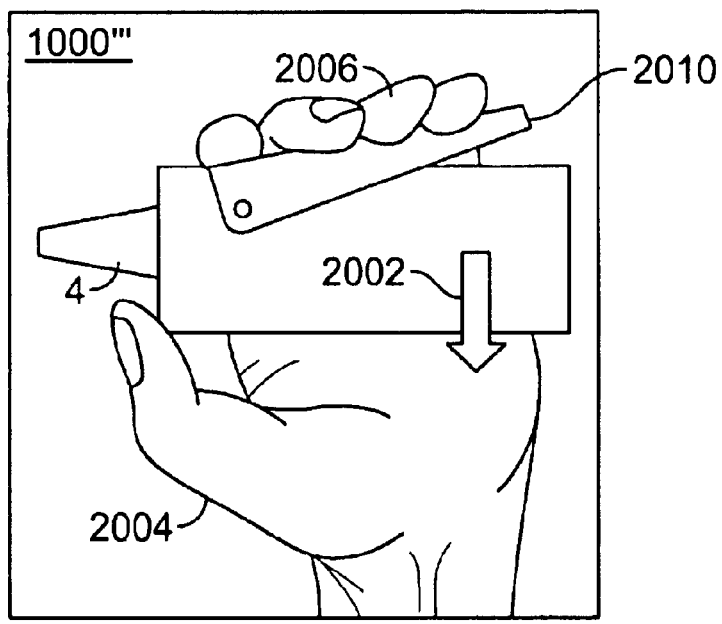
FIGS. 16(a) to FIGS. 16(c) show variations on a drug dispenser according to an embodiment of the present invention where a lever actuates the sachet driving mechanism.
Figure 16B:
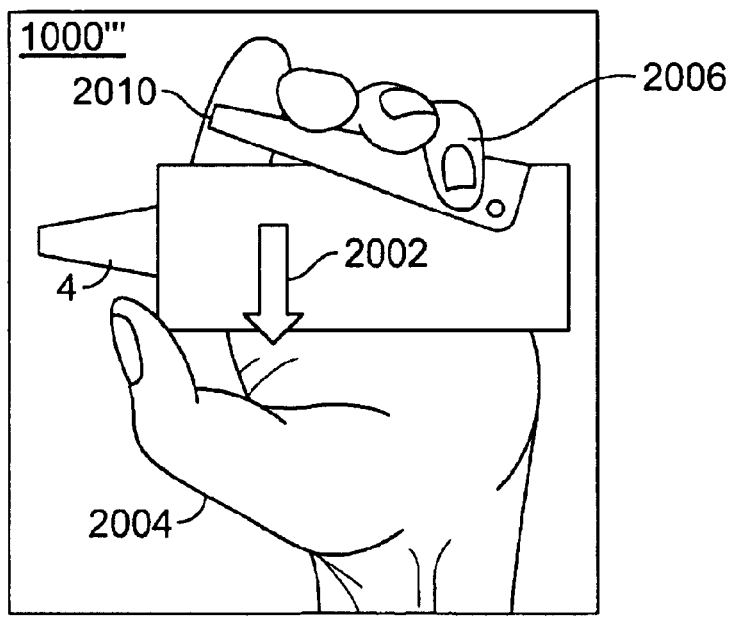
Figure 16C:
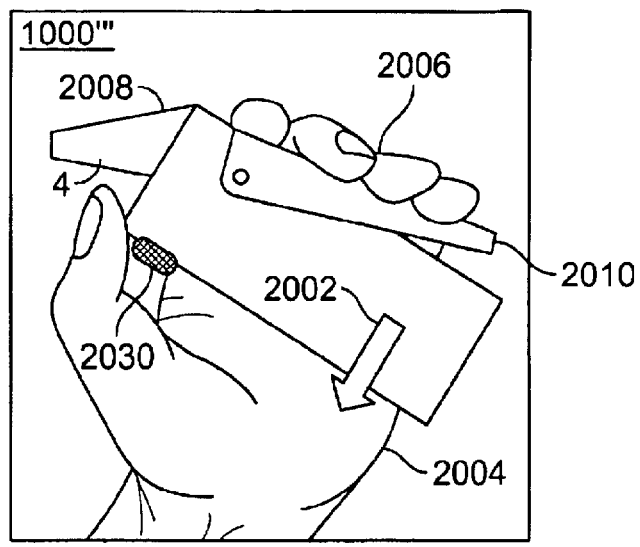

FIG. 16(a) to FIG. 16(c) show devices 1000''' according to alternative embodiments of the present invention, wherein the actuator 14 is a lever 2010. In each figure, lever 2010 is depressed in the direction of arrow 2002 to drive a sachet advance mechanism 25 (not shown). FIG. 16(a) shows the lever 2010 with its free end at the rear of the device 1000''' where the fingers 2006 of a human hand 2004 depress the lever 2010. FIG. 16(b) shows the free end of the lever 2010 at the front of the device 1000''', and FIG. 16(c) shows the lever 2010 with the free end at the rear of the device 1000''' with a dispensing portion 2004 angled downward for an improved ergonomic design. In each case, the device is acutated by the user squeezing the lever 2010 towards the housing of the device as shown.

Using a lever to actuate the sachet advance mechanism 25 of the device is advantageous to geriatric patients with weakened hand muscles from the onset of arthritis and other conditions associated with old age that weaken motor function. The lever provides added leverage to reduce the amount of force needed to drive the sachet advance mechanism.

Figure 17:
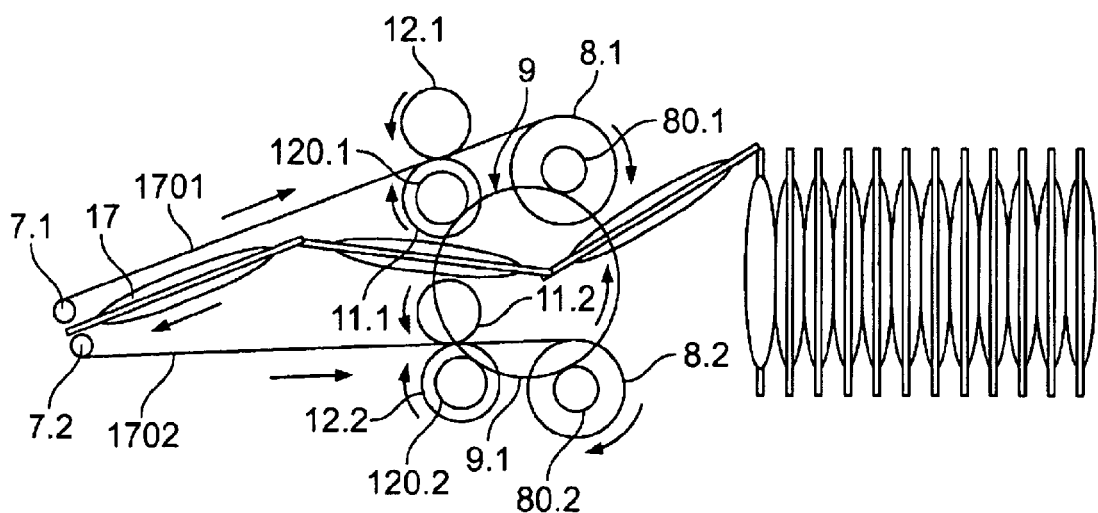
FIG. 17 shows an illustrative sachet advance mechanism and sachet pack that can be used in conjunction with the devices of FIGS. 16(a) through 16(c).

FIG. 17 shows an illustrative sachet advance mechanism 25 for the embodiments of FIGS. 16(a)–16(c), with similar components bearing similar reference numerals as FIGS. 1–15. Referring to FIG. 17, the the continuous sachet sheet is fed towards rollers 7.1, 7.2. After the continuous sheet passes through roller 7.2, strip 1702 is wrapped around roller 7.2 and is fed into a nip formed between rollers 12.2 and 11.2, and strip 1701 is wrapped around roller 7.1 and is fed into a nip formed between rollers 12.1 and 11.1. After exiting the nip formed between rollers 12.1, 11.1, strip 1701 is wrapped around waste roller 8.1, and after exiting the nip formed between rollers 12.2, 11.2, strip 1702 is wrapped around waste roller 8.2. Gear 9 is engaged with gears 120.1, 120.2, 80.1, and 80.2 which drive rollers 11.1, 11.2, 8.1 and 8.2 respectively.

Figure 18:
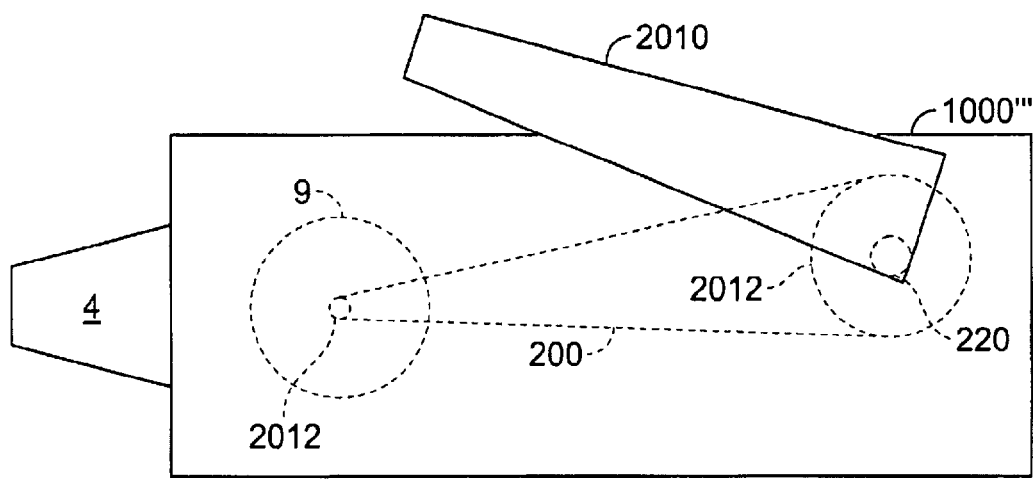
FIG. 18 shows an illustrative pulley, belt, and clutch arrangement for connecting the lever and gear of the device of FIG. 16(b).

FIG. 18 shows the device 1000''' of FIG. 16(b) with the free end of the lever 2010 at the front of the device 1000'''. The other end of the lever 2010 is coupled to a clutch 220 that turns in one direction to drive the gear 9 via belt 200 and pulleys 2012. When pressure is applied to the lever 2010, the clutch 220 is turned, driving the belt 200 to turn the main gear 9. Although a belt and pulley arrangement is shown, it should be understood that the pulley and belt could be replaced with a sprocket and chain, respectively. Alternatively, the pulley and belt could be repaced with a linkage arrangement or a gear arrangement. For ease of illustration, only the gear 9 of the sachet advance mechanism of FIG. 17 is shown in FIG. 18. Preferably, the clutch 220 and pulleys 2012 are sized so that each full depression of the lever 2010 turns the gear 9 by an amount sufficient to cause a unit dose of medicament to be delivered through mouthpiece 4. Preferably, the mouthpiece 4 is of the type discussed above with regard to FIGS. 6, 10, 11, 13, and 14.

Figure 19:
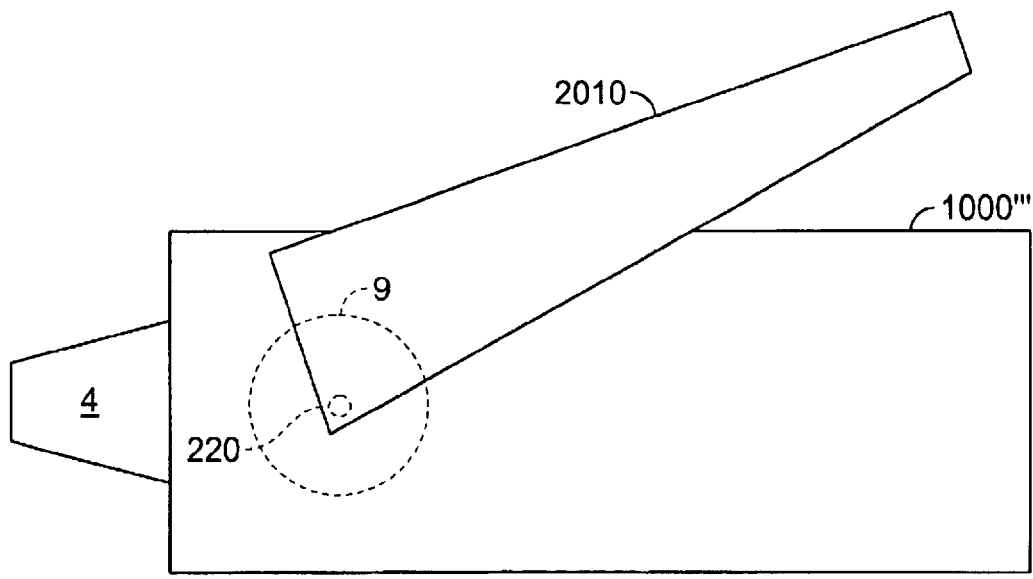
FIG. 19 shows a clutch arrangement for connecting the lever and gear connection of the devices of FIGS. 16(a) and (c).

FIG. 19 shows the drug dispenser of FIGS. 16(a) and 16(c) where the free end of the lever 2010 is at the rear of the device 1000'''. The lever 2010 is connected directly to the main gear 9 via a one-way clutch 220 that causes the gear 9 to turn in one direction upon depressing the lever 2010, thereby turning the gears of the sachet drive mechanism as previously discussed.

FIGS. 20(a–c) show a particularly preferred acutation mechanism for the embodiment of FIG. 17. In this embodiment, the main gear 9 includes a plurality of receptacles 9.9 (in this case, three) which are configured to receive end 204 of a drive arm 201. Drive arm 201 includes a first member 201.1 and a second member 201.2 interconnected via a free linkage 203. The free end of second member 201.2 is secured to the housing via a fixed point linkage 202. The free end 204 of the first member 201.1 of the drive arm 201 is configured to engage the receptables 9.9 as described above.

In operation, a user lifts the lever 2010. Preferably, an overcentre spring (not shown) normally holds the lever 2010 down, so that a small amount of force is required to lift the lever, and thereafter, the lever 2010 will rise to the upward position shown in FIGS. 16(a–c). The user can push the lever 2010 up and down freely. However, when the lever is pushed completely down it will be held down by the overcentre spring. The lever 2010 is coupled to free linkage 203 so that when the lever 2010 rises to the position shown in FIGS. 16(a–c), the drive arm 201 is in the position shown in FIGS. 20(a) and 20(c), and when the lever is pushed completely down, the drive arm is in the position shown in FIG. 20(b).

Figure 20A:
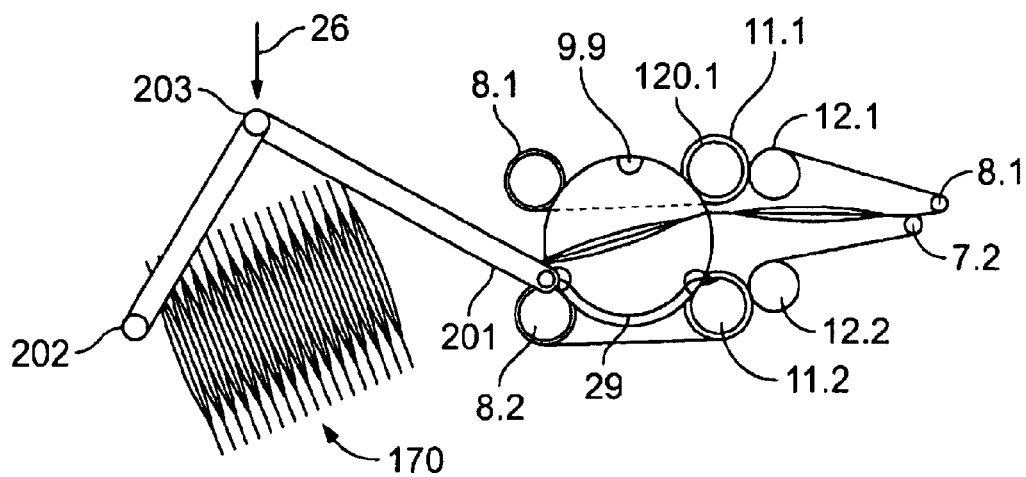
FIGS. 20(a–c) show a preferred acutation mechanism for the embodiment of FIG. 17.
Figure 20B:
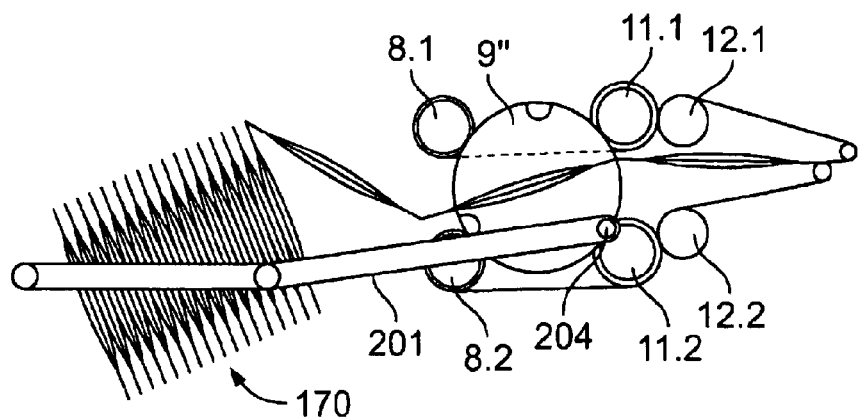
Figure 20C:
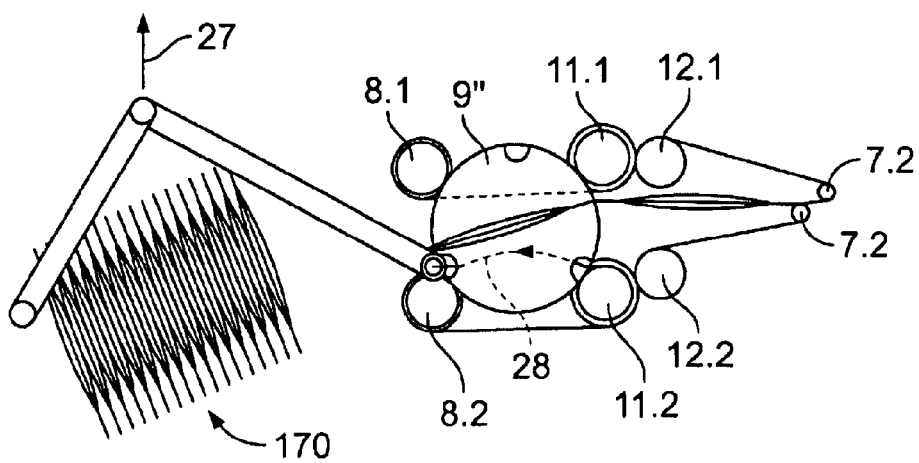

A safety button 2030 (shown only in FIG. 16(a) for ease of illustration) may also provided to prevent accidental actuation of the device of FIGS. 16(a–c). Referring to FIG. 20(a), when the lever 2010 is in its upward position (as shown FIGS. 16a–c), and the button 2030 is pressed, end 204 of drive arm 201 becomes engaged with adjacent receptacle 9.9. Thereafter, if the linkage 203 of the drive arm 201 moves in the direction 26 under the impetus of lever 2010, the drive arm 201 will follow path 29 to the position shown in FIG. 20(b), thereby rotating gear 9 by approximately 120 degrees, and opening one of the sachets 17. When the drive arm 201 reaches the position shown in FIG. 20(b), end 204 becomes disengaged from the receptacle 9.9, so that when the linkage 203 of the drive arm 201 subsequently moves upward in the direction 27 under the impetus of lever 20 10, the drive arm 201 follows the path 28 shown in dotted lines as shown in FIG. 20(c), without causing further rotation of the drive gear 9. If the button 2030 were to be subsequently pressed, end 204 of drive arm 201 would become engaged with the now adjacent receptable 9.9.

In this regard, the path 28 could be defined, for example, by a slot on an interior surface of the housing which engages an outwardly facing protrusion on the end 204 of drive arm 201. In such an embodiment, the end 204 could also include an inwardly facing protrusion which is engagable with the receptable 9.9. The safety button 2030, when pressed, could move the end 204 towards the gear 9.9, thereby bringing the end 204 into engagement with the receptable, and thereby preventing the end 204 from engaging the slot as it moves in the direction 29. As one of ordinary skill in the art will appreciate, however, alternative techniques could also be used to implement the drive arm movement illustrated in FIGS. 20(a–c).

It should be noted that although the safety button 2030 is illustrated in connection with the embodiment of FIG. 16(a–c), this feature can also be incorporated into the other embodiments of the present invention which are described herein. In this regard, a safety button 2030 could be provided in any of the embodiments described above, to prevent accidental actuation of the device (e.g., by dropping the device), or actuation by a child.

For example, the saftey button 2030.could be interconnected between actuator 14 of FIG. 1 and gear 9 to prevent actuation of acuator 14 from causing the device to release medicament, absent prior actuation of the safety button. Similarly, in the device of FIG. 6, the saftey button 2030 could be interconnected between actuator 14' and gear 9.1, between gear 9.2 and gear 9.3, between lever 5.1 and gear 9.2, or between cover hinge 9.21 and torsion spring 9.22, to prevent actuation of acuator 14 from causing the device to release medicament, absent prior actuation of the safety button. In the embodiment of FIG. 11, for example, the saftey button 2030 could be interconnected between actuator 14' and gear 9.1, between gear 9.2 and gear 9.3, between actuator 500 and gear 9.2, or between cover hinge 9.21 and torsion spring 9.22, to prevent actuation of acuator 14' from causing the device to release medicament, absent prior actuation of the safety button. In the embodiment of FIG. 12, for example, the safety button 2030 could be interconnected between actuator 14" and rollers 8.1" and 8.2". In the embodiment of FIG. 18, the safety button 2030 could, for example, be interconnected between the lever 2010 and the clutch 220 or gear 9, and in the embodiment of FIG. 19, the safety button 2030 could, for example, be interconnected between the lever 2010 and the clutch 220. Other arrangements will also be apparent to those skilled in the art.

In certain embodiments of the present invention, a dose counter 36 (for ease illustration, shown only in FIG. 10) may be disposed within the housing.

The dose counter 36 may be coupled to actuator 14, 14', 14" of FIGS. 1–20, to the sachet advance mechanism 25 of FIG. 1, to the sachet drive mechanism 20 of FIGS. 3–5, to the chassis 3' and associated components of FIGS. 6–11, or to the chassis 3" and associated components of FIGS. 12–13, to count the number of unit doses that have been dispensed by the drug delivery device over time. Such a dose counter 36 may be of a mechanical or electrical design, as is known in the art.

In a particularly preferred embodiment, however, the dose counter 36 may simply comprise a transparent window in the housing which is disposed in the path of one of the strips 1701, 1702, downstream of the separation point of the first and second strips (e.g., downstream of the rollers 7). In such an embodiment, the dose count could simply be imprinted on the interior surface of one of the strips 1701, 1702. As an example, the number 2 could be imprinted on the interior surface of strip 1701 of a first sachet 17 in the sachet pack 170, with subsequent sachets sequentially numbered, so that when the second sachet 17 in the sachet pack 170 is the next dose to be delivered, the number 2 will be visible through the dose counter 36. The number 1, in turn, could be imprinted on the interior surface 1701 of lead section of the sachet pack 170 so that, prior to its first use, the number 1 is visible through the dose counter 36.

As noted above, the drug delivery devices in accordance with the various embodiments of the present invention are designed to store multiple doses of a medicament, and to deliver a unit dose of the medicament into the oral cavity of a patient for gastrointestinal (e.g., gastric, intestinal, and/or colonic) absorption or action; esophageal absorption or action; and/or absorption or action in the oral cavity (e.g., sublingual, lingual, or buccal). The medicament may be in the form of a solid, semi-solid, or liquid.

Exemplary medicaments which can be delivered into the oral cavity of a patient in accordance with the various embodiments of the present invention are described in WO 01/64182, entitled "Improvements In or Relating to the Delivery of Oral Drugs", published Sep. 9, 2001, and U.S. Provisional Application Ser. No. 60/317,522, filed Sep. 5, 2001, entitled "Functional Powders for Oral Delivery", the entire disclosures of each of which are hereby incorporated by reference.

Preferably, when the medicament is a solid, the medicament comprises drug particles greater than 10 microns in order to minimize the inhalation of the drug particles into the lungs, in order to have substantially all of the dose deposited in the gastrointestinal system. The mean drug particle size of the unit dose is greater than 10 $\mu$m and preferably greater than about 50 $\mu$m in order to minimize pulmonary aspiration of the drug such that an effective dose of said drug cannot be delivered into the lower lung of a human patient. For example, the drug particles can be greater than about 75 $\mu$m, or greater than about 100 $\mu$m. A preferred range of the mean drug particle size is about 100 $\mu$m to about 500 $\mu$m, although drug particles of 1 mm and above would still be functional in the present invention. Preferably, any inactive particle in the unit dose is also greater than 10 $\mu$m in order to minimize pulmonary aspiration of such particles.

In order to achieve the desired mean particle size, the active material can be incorporated into larger particles if the active agent itself is less than 10 $\mu$m. This can be performed by known procedures in the art, e.g., by granulation, coating, agglomeration or spray coating. The larger particles may include excipients suitable for use in pharmaceutical formulations.

In preferred embodiments of the invention, the mean drug particle size of the multiparticulates does not vary by more than about 20%, more preferably no more than about 15% and most preferably by no more than about 10%. Preferably, any inactive particles will also be within this range.

In preferred embodiments, greater than about 80% of the drug particles fall within the above disclosed variance, more preferably greater than 90% and most preferably about 100% of the drug particles fall within the above disclosed ranges. For example, in a preferred embodiment, about 90% of the drug particles of the unit dose would have a mean particle size of about 450 to about 550 μm, although this example is not meant to be limiting. Preferably, any inactive particles also fall within this range.

The size of the unit dose is dependent on the amount of drug needed to provide the intended therapeutic effect and the amount of any pharmaceutically acceptable excipient which may be necessary. Typically, a unit dose of from about 0.01 mg to about 1.5 g would be sufficient to contain a therapeutically effective amount of the drug to be delivered, however, this range is not limiting and can be smaller or higher, depending on the amount of drug and excipient that is necessary. Generally, the unit dose should not be so large that it is not capable of being swallowed by the patient without much difficulty. It is preferred that the unit dose is of a small enough quantity that it can be swallowed without the necessity, of an additional liquid, however, the invention is not limited to such quantity and doses which may require a liquid are contemplated by the invention.

Preferably the unit dose is from about 1 mg to about 100 mg, or from about 10 mg to about 50 mg, depending on the potency of the active agent. In situations where the unit dose is too large to be easily swallowed, it is contemplated that the system can be actuated multiple times for subsequent delivery in order to administer divided doses of the intended dose, which are more easily swallowed by the patient.

When it is contemplated for the unit dose to be swallowed without the use of an additional liquid, certain embodiments of the invention provide that the multiparticulates comprise an effective amount of an agent which stimulates the production of saliva in order to facilitate the swallowing of the unit dose. Such agents include any acid which is safe for human consumption and includes food acids, acid anhydrides and acid salts. Food acids include tartaric acid, malic acid, fumaric acid, adipic acid, and succinic acids and fruit acids, e.g., citric acid. Acid anhydrides of the above described acids may also be used. Acid salts may include sodium, dihydrogen phosphate, disodium dihydrogen pyrophosphate, acid citrate salts and sodium acid sulfite.

In other embodiments of the invention, the multiparticulates can comprise an effervescent compound or composition which provides a pleasing organoleptic effect which can substantially mask the taste of unpalatable active ingredients in the powder. The effervescent action also acts as a stimulant to saliva production. Effervescent agents include compounds which evolve gas. The preferred effervescent agents evolve gas by means of chemical reactions which take place upon exposure to a liquid such as saliva in the mouth.

This bubble or gas generating chemical reaction is most often the result of the reaction of an acid (e.g. the saliva stimulant acids listed above) and an alkali metal carbonate/dicarbonate or base. The reaction of these two general classes of compounds produces carbon dioxide gas upon contact with saliva.

The use of acids and/or effervescent ingredients is particularly useful in patients with achlorhydria or other patients with a problem swallowing the unit dose without the use of a liquid.

As with most pharmaceutical formulations, it is often necessary to add a pharmaceutically acceptable excipient to the drug. For example, when formulating an agent into tablets or capsules, a bulking agent is used in order to provide enough mass to tablet or capsule the agent. This results in many of the drawbacks of solid dosage forms which were discussed above.

With the present invention, however, it is not necessary to have a large percent of the formulation consisting of excipient as it is preferable to have the unit dose which is deposited on the tongue of the patient as small as possible in order to facilitate swallowing. The use of excipient is used in the present invention, e.g., to improve flowability, to taste mask, to stimulate flow of saliva for swallowing or to provided a modified release of the drug. In preferred embodiments the excipient is less than about 20% by weight of the multiparticulates and more preferably less than about 10% by weight of the multiparticulates. These preferred percent weights of excipients are not meant to be limiting. For example, with a micro-dose drug such as digoxin or levothyroxine, the percent of excipient may need to be more than 20% in order to provide enough bulk for acceptable flow or dose metering characteristics.

The pharmaceutical acceptable excipient of the multiparticulates can coat the drug. In such an embodiment, the excipient can provide a modified release of the drug. For example, such a multiparticulate can be formulated to provide a delayed release wherein the drug is released in the intestine. Multiparticulate with an excipient coating can also be formulated in order to provide a sustained release of the drug over time in the gastrointestinal tract. Coating the drug with excipient can also be done in order to mask the bitter taste of certain drugs. Alternatively, the excipient can be used as a substrate and the drug can be coated onto the excipient. This formulation option can be used in order to provide desired flow capabilities and to provide a critical mass of the drug particles in order to minimize lung aspiration. The excipient can also be used in a mixture with the drug in order to provide the desired properties (e.g., flow properties) to allow the unit dose to be delivered as a discreet unit, with minimal multiparticulates suspended in the air.

When the multiparticulates are formulated as controlled release powders, the drug may be combined with a polymer which may be soluble, insoluble, permeable, impermeable or biodegradable. The polymers may be polymers or copolymers. The polymer may be a natural or synthetic polymer. Natural polymers include polypeptides, polysaccharides and alginic acid. A suitable polypeptide is zein and a suitable polysaccharide is cellulose. The drug/polymer combination can be formed by known methods such as granulating, spray coating or agglomerating.

Representative synthetic polymers include alkyl celluloses, hydroxyalkyl celluloses, cellulose ethers, cellulose esters, nitro celluloses, polymers of acrylic and methacrylic acids and esters thereof, polyamides, polycarbonates, polyalkylenes, polyalkylene glycols, polyalkylene oxides, polyalkylene terephthalates, polyvinyl alcohols, polyvinyl ethers, polyvinyl esters, polyvinyl halides, polyvinylpyrrolidone, polyglycolides, polysiloxanes and polyurethanes and co-polymers thereof. The polymer to be used is governed by its toxicity and its compatibility with the particular active ingredient being used and can be selected without difficulty by those skilled in the art.

Particularly suitable polymers include: methyl cellulose, ethyl cellulose, hydroxypropyl cellulose, hydroxypropyl methyl cellulose, hydroxybutyl methyl cellulose, cellulose acetate, cellulose propionate (lower, medium or higher molecular weight), cellulose acetate propionate, cellulose acetate butyrate, cellulose acetate phthalate, carboxymethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), poly(ethylene), poly (ethylene) low density, poly(ethylene) high density, poly(propylene), poly(ethylene glycol), poly(ethylene oxide), poly(ethylene terephthalate), poly(vinyl alcohol), poly(vinyl isobutyl ether), poly(vinyl acetate), poly(vinyl chloride) and polyvinylpyrrolidone.

Especially suitable co-polymers include: butyl methacrylate/isobutyl methacrylate co-polymer, high molecular weight, methylvinyl ether/maleic acid co-polymer, methylvinyl ether/maleic acid, monoethyl ester co-polymer, methylvinyl ether/maleic anhydride co-polymer and vinyl alcohol/vinyl acetate co-polymer.

Representative biodegradable polymers include, polytactides, polyglycolides, poly(ethylene terephthalate), polyhydroxy-butyrate, polyhydroxy-valerate and polyurethane.

Representative acrylates and methacrylates are poly-acrylic and methacrylic polymers such as those sold under the Trademarks Eudragit. Amberlite and Carbopol.

Classes of drugs which are suitable in the present invention include antacids, anti-inflammatory substances, coronary dilators, cerebral dilators, peripheral vasodilators, anti-infectives, psychotropics, anti-manics, stimulants, antihistamines, laxatives, decongestants, vitamins, gastrointestinal sedatives, anti-diarrheal preparations, anti-anginal drugs, vasodilators, anti-arrhythmics, anti-hypertensive drugs, vasoconstrictors and migraine treatments, anti-coagulants and anti-thrombotic drugs, analgesics, anti-pyretics, hypnotics, sedatives, anti-emetics, anti-nauseants, anti-convulsants, neuromuscular drugs, hyper- and hypoglycemic agents, thyroid and anti-thyroid preparations, diuretics, anti-spasmodics, uterine relaxants, mineral and nutritional additives, anti-obesity drugs, anabolic drugs, erythropoietic drugs, anti-asthmatics, bronchodilators, expectorants, cough suppressants, mucolytics, drugs affecting calcification and bone turnover and anti-uricemic drugs.

Specific drugs include gastro-intestinal sedatives such as metoclopramide and propantheline bromide; antacids such as aluminum trisilicate, aluminum hydroxide, ranitidine and cimetidine; anti-inflammatory drugs such as phenylbutazone, indomethacin, naproxen, ibuprofen, flurbiprofen, diclofenac, dexamethasone, prednisone and prednisolone; coronary vasodilator drugs such as glyceryl trinitrate, isosorbide dinitrate and pentaerythritol tetranitrate; peripheral and cerebral vasodilators such as sotoctidilum, vincamine, naftidrofuryl oxalate, co-dergocrine mesylate, cyclandelate, papaverine and nicotinic acid; anti-infective substances such as erythromycin stearate, cephalexin, nalidixic acid, tetracycline hydrochloride, ampicillin, flucloxacillin sodium, hexamine mandelate and hexamine hippurate; neuroleptic drugs such as flurazepam, diazepam, temazepam, amitryptyline, doxepin, lithium carbonate, lithium sulfate, chlorpromazine, thioridazine, trifluperazine, fluphenazine, piperothiazine, haloperidol, maprotiline hydrochloride, imipramine and desmethylimipramine; central nervous stimulants such as methylphenidate, ephedrine, epinephrine, isoproterenol, amphetamine sulfate and amphetanine hydrochloride; antihistamic drugs such as diphenhydramine, diphenylpyraline, chlorpheniramine and brompheniramine; anti-diarrheal drugs such as bisacodyl and magnesium hydroxide; the laxative drug, dioctyl sodium sulfosuccinate; nutritional supplements such as ascorbic acid, alpha tocopherol, thiamine and pyridoxine; anti-spasmodic drugs such as dicyclomine and diphenoxylate; drugs affecting the rhythm of the heart such as verapamil, nifedipine, diltiazem, procainamide, disopyramide, bretylium tosylate, quinidine sulfate and quinidine gluconate; drugs used in the treatment of hypertension such as propranolol hydrochloride, guanethidine monosulphate, methyldopa, oxprenolol hydrochloride, captopril and hydralazine; drugs used in the treatment of migraine such as ergotamine; drugs affecting coagulability of blood such as epsilon aminocaproic acid and protamine sulfate; analgesic drugs such as acetylsalicylic acid, acetaminophen, codeine phosphate, codeine sulfate, oxycodone, dihydrocodeine tartrate, oxycodeinone, morphine, heroin, nalbuphine, butorphanol tartrate, pentazocine hydrochloride, cyclazacine, pethidine, buprenorphine, scopolamine and mefenainic acid; anti-epileptic drugs such as phenytoin sodium and sodium valproate; neuromuscular drugs such as dantrotene sodium; substances used in the treatment of diabetes such as tolbutamide, disbenase glucagon and insulin; drugs used in the treatment of thyroid gland dysfunction such as triiodothyronine, thyroxine and propylthiouracil, diuretic drugs such as furosemide, chlorthalidone, hydrochlorthiazide, spironolactone and triamterene; the uterine relaxant drug ritodrine; appetite suppressants such as fenfluramine hydrochloride, phentermine and diethylproprion hydrochloride; anti-asthmatic and bronchodilator drugs such as aminophylline, theophylline, salbutamol, orciprenaline sulphate and terbutaline sulphate; expectorant drugs such as guaiphenesin; cough suppressants such as dextromethorphan and noscapine; mucolytic drugs such as carbocisteine; anti-septics such as cetylpyridinium chloride, tyrothricin and chlorhexidine; decongestant drugs such as phenylpropanolamine and pseudoephedrine; hypnotic drugs such as dichloralphenazone and nitrazepam; anti-nauseant drugs such as promethazine theoclate; haemopoietic drugs such as ferrous sulphate, folic acid and calcium gluconate; uricosuric drugs such as sulphinpyrazone, allopurinol and probenecid; and calcification affecting agents such as biphosphonates, e.g., etidronate, pamidronate, alendronate, residronate, teludronate, clodronate and alondronate.

Drugs which possess taste and/or odor characteristics which, when administered orally without any excipients, render the drug or therapeutic agent unpalatable to a subject and would be candidates for taste masking in the present invention include, but are not limited to, $H_2$ receptor antagonists, antibiotics, analgesics, cardiovascular agents, peptides or proteins, hormones, anti-migraine agents, anti-coagulant agents, anti-emetic agents, anti-hypertensive agents, narcotic antagonists, chelating agents, anti-anginal agents, chemotherapy agents, sedatives, anti-neoplastics, prostaglandins, antidiuretic agents and the like. Typical drugs include but are not limited to nizatidine, cimetidine, ranitidine, famotidine, roxatidine, etinidine, lupitidine, nifentidine, niperitone, sulfotidine, tuvatidine, zaltidine, erythomycin, penicillin, ampicillin, roxithromycin, clarithromycin, psylium, ciprofloxacin, theophylline, nifedipine, prednisone, prednisolone, ketoprofen, acetaminophen, ibuprofen, dexibuprofen lysinate, flurbiprofen, naproxen, codeine, morphine, sodium diclofenac, acetylsalicylic acid, caffeine, pseudoephedrine, phenylpropanolamine, diphenhydramine, chlorpheniramine, dextromethorphan, berberine, loperamide, mefenamic acid, flufenamic acid, astemizole, terfenadine, certirizine, phenytoin, guafenesin, N-acetylprocainamide HCl, pharmaceutically acceptable salts thereof and derivatives thereof.

The devices in accordance with embodiments of the present invention are particularly useful for delivering fast melt formulations, such as those described in U.S. patent application Ser. No. 10/383,351, filed Mar. 7, 2003, entitled "FAST MELT MULTIPARTICULATE FORMUALTIONS FOR ORAL DELIVERY," (Attorney Docket No. 478.1023US) the entire disclosure of which is hereby incorporated by reference. A fast melt formulation, as defined herein, is a formulation which dissolves or disperses in a patient's mouth within 1 minute after administration without the coadministration of a fluid. Preferably, the formulation dissolves or disperses in a patient's mouth within 30 seconds, or 15 seconds after administration without the coadministration of a fluid. In this regard, the term "disperses" means that the administered formulation becomes hydrated in the mouth and the particles of the formulation become suspended is saliva, such that the multiparticulate formulation is wetted and easily swallowed.

The effect of humidity can have a negative impact of the flowability of particles (e.g., due to cohesiveness). This can be a particular problem with respect to fast melt formulations which are designed to absorb water. Accordingly, the mulitple dose sachet delivery devices in accordance with embodiments of the present invention are particularly useful for the delivery of fast melt formulations, becauase the unit doses are premetered prior to actuation of the device. This reduces the contamination of the unit doses as compared to having the formulation in a multiple dose reservoir. Moreover, providing the premetered unit doses in sachets (which are sealed) minimizes the effect of humidity and moisture on the formulation.

In certain embodiments, the fast melt formulation is a drug formulation for gastrointestinal deposition comprising a non-compressed free flowing plurality of particles comprising an active agent and a water-soluble excipient, the particles having a mean diameter of greater than 10 µm to about 1 mm, the particles comprising at least about 50% drug and the formulation dissolving or dispersing in a patient's mouth within 1 minute after administration without the coadministration of a fluid.

In other embodiments, the devices described herein are used to treat a patient with an active agent for gastrointestinal deposition by administering a fast melt formulation comprising a non-compressed free flowing plurality of particles comprising an active agent and a water-soluble excipient, the particles having a mean diameter of greater than 10 µm to about 1 mm, and the formulation dissolving or dispersing in a patient's mouth within 1 minute after administration without the coadministration of a fluid.

The water-soluble excipient of the fast melt formulation can be a sugar alcohol including, but not limited to sorbitol, mannitol, maltitol, reduced starch saccharide, xylitol, reduced paratinose, erythritol, and combination thereof. Other suitable water-soluble excipients include gelatin, partially hydrolyed gelatin, hydrolyzed dextran, dextrin, alginate and mixtures thereof.

The fast melt formulations preferably include a salivary stimulant including, but not limited to citric acid, tartaric acid, malic acid, fumaric acid, adipic acid, succinic acid, acid anhydrides thereof, acid salts thereof and combinations thereof. The salivary stimulant can also be an effervescent agent, such as wherein the effervescence is the result of a reaction of a soluble acid source and an alkali metal carbonate or carbonate source. The carbonate sources can be selected from the group consisting of dry solid carbonate and bicarbonate salts such as sodium bicarbonate, sodium carbonate, potassium bicarbonate and potassium carbonate, magnesium carbonate and sodium sesquicarbonate, sodium glycine carbonate, L-lysine carbonate, arginine carbonate and amorphous calcium carbonate.

The fast melt formulations preferably comprise a sweetener such as a water-soluble artificial sweetener, including but not limited to soluble saccharin salts, such as sodium or calcium saccharin salts, cyclamate salts, acesulfam-K, the free acid form of saccharin and mixtures thereof. The sweetener can also comprise a dipeptide based sweetener such as L-aspartyl L-phenytalanine methyl ester. The fast melt formulations can also comprise further pharmaceutical excipients such as polyvinyl alcohol, polyvinylpyrrolidine, acacia or a combination thereof.

The dissolution or dispersion of the fast melt formulation can be improved with the use of a surfactant, such as sodium lauryl sulphate (Texapon K 12), various polysorbates known under the trade name Tween, ethers of polyhydroxy ethylene fatty acids known under the trade name Brij, esters of polyhydroxy ethylene fatty acids known under the trade name Myrj, sodium desoxycholate, glycerol polyethylene glycol ricinoleate (Cremophor EL), polyoxyethylene-polyoxypropylene polymers known under the trade name Pluronic, and various polyalkoxy alkylene sterol ethers.

The fast melt formulations can also comprise starches, e.g., corn starch, or modified starches, e.g., sodium starch glycolate or mixtures thereof, in any proportions. Starches can provide increased salivation due to the porous nature of the starch. Increased salivation favors rapid dissolution or dispersion of the formulation upon oral administration.

When a starch is present in the formulation, the formulation can further comprise a starch degrading enzyme will have a synergistic effect with the starch with respect to dissolution or dispersion. The enzymes upon being contacted with an aqueous solution will initiate conversion of the starch to mono and polysaccharides which quickly dissolve in the aqueous environment and further contribute to improving the taste of the multiparticulate formulation and increasing salivation. The enzymes can be chosen for their degradation effect on the starch and also for their stability over time, i.e. during the shelf-life of the fast melt multiparticulate formulation. Advantageously, the enzyme will be chosen from the group of starch degrading enzymes comprising alpha-amylase, beta-amylase, amyloglucosidase, debranching enzymes and glucose-fructose isomerase. In certain embodiments, the enzymes can be an equal mixture of amyloglucosidase and a-amytase.

In certain embodiments, the fast melt formulations for gastrointestinal deposition are prepared by a process comprising melt granulating the water soluble excipient and the active agent to form a homogenous mixture. In an alternate embodiment, the process comprises melt coating the water-soluble excipient onto the active agent which can be optionally pregranulated with a pharmaceutically acceptable excipient. In such processes, the water-soluble excipient is a water-soluble alcohol such as xylitol.

The melt granulation and melt coating processes are particularly preferred as it is not necessary to use an aqueous fluid as a processing aid. This results in a process which can be used for a wide variety of active agents, including those agents which would be susceptible to degradation upon contact with water. Accordingly, such processes provide advantages over many prior art processes for making fast melt systems which rely on water as a processing aid. These prior art processes would not be suitable for water liable drugs as such processes would result in degradation of the drug during the manufacturing process and during storage due to residual moisture in the final product.

Any of the active agents described above can also be used in accordance with fast melt formulations. However, particularly preferred agents for fast melt formulations include antibiotics such as clarithromycin, amoxicillin erythromycin, ampicillin, penicillin, cephalosporins, e.g., cephalexin, pharmaceutically acceptable salts thereof and derivatives thereof. Other preferred agents are acetaminophen and NSAIDS such as ibuprofen, indomethacin, aspirin, diclofenac and pharmaceutically acceptable salts thereof.

The size of the unit dose of the fast melt formulations is dependent on the amount of drug needed to provide the intended therapeutic effect and the amount of any pharmaceutically acceptable excipient which may be necessary. Typically, a unit dose of from about 0.01 mg to about 1.5 g would be sufficient to contain a therapeutically effective amount of the drug to be delivered, however, this range is not limiting and can be smaller or higher, depending on the amount of drug and excipient that is necessary In the preceding specification, the invention has been described with reference to specific exemplary embodiments and examples thereof. It will, however, be evident that various modifications and changes may be made thereto without departing from the broader spirit and scope of the invention as set forth in the claims that follow. The specification and drawings are accordingly to be regarded in an illustrative manner rather than a restrictive sense.

What is claimed is:

1. A delivery device, comprising:
    a sachet pack including a plurality of unit doses of a medicament enclosed between a first strip and a second strip;
    a first member;
    a second member;
    an actuator, the actuator pulling the first strip against the first member and the second strip against the second member to release a unit dose of the medicament from the sachet pack; and
    a mouthpiece positioned relative to the sachet pack, the first member, and the second member, to deliver the unit dose of the medicament to an oral cavity of a patient, wherein the actuator includes
    an actuator input;
    a first pair of index rollers defining a first nip therebetween, the first strip passing through the first nip;
    a second pair of index rollers defining a second nip therebetween, the second strip passing though the second nip; and
    a drive coupled to the actuator input, the first pair of index rollers and the second pair of index rollers;
    and wherein upon actuation of the actuator input by a patient, the drive causes rotation of the first and second pairs of index rollers, which in turn, pull a portion of the first and second strips through the first and second nips, respectively.

2. The device of claim 1, wherein the drive comprises a gear, the gear engaging one of the first pair of index rollers and one of the second pair of index rollers, the gear being coupled to the actuator input such that actuation of the actuator input causes a predetermined rotation of the gear.

3. A delivery device, comprising:
    a sachet pack including a plurality of unit doses of a medicament enclosed between a first strip and a second strip;
    a first roller spaced apart forward from a second roller, the first strip being wrapped around the first roller, the second strip being wrapped around the second roller;
    an actuator, the actuator, upon actuation by a patient, pulling the first strip around the first roller and pulling the second strip around the second roller to release a unit dose of the medicament from the satchet pack; and
    a mouthpiece positioned relative to the sachet pack, the first roller, and the second roller, to deliver the unit dose of the medicament to an oral cavity of the patient, wherein the actuator includes
    an actuator input;
    a first pair of index rollers defining a first nip therebetween, the first strip passing through the first nip;
    a second pair of index rollers defining a second nip therebetween, the second strip passing though the second nip; and
    a drive coupled to the actuator input, the first pair of index rollers and the second pair of index rollers;
    and wherein upon actuation of the actuator input by a patient, the drive causes rotation of the first and second pairs of index rollers, which in turn, pull a portion of the first and second strips through the first and second nips, respectively.

4. The device of claim 3, wherein the drive comprises a gear, the gear engaging one of the first pair of index rollers and one of the second pair of index rollers, the gear being coupled to the actuator input such each actuation of the actuator input causes a predetermined rotation of the gear.

5. A delivery device, comprising:
    a sachet pack including a plurality of unit doses of a medicament enclosed between a first strip and a second strip;
    a first roller spaced apart forward from and above a second roller, the first strip being wrapped around the first roller, the second strip being wrapped around the second roller;
    an actuator, the actuator, upon actuation by a patient, pulling the first strip around the first roller and pulling the second strip around the second roller to release a unit dose of the medicament from the sachet pack; and
    a mouthpiece surrounding the first and second rollers, the mouthpiece having a top surface, a bottom surface, and a pair of lateral surfaces, the bottom surface having an opening formed therein, the released medicament passing through the opening, wherein the actuator includes
    an actuator input;
    a first pair of index rollers defining a first nip therebetween, the first strip passing through the first nip;
    a second pair of index rollers defining a second nip therebetween, the second strip passing though the second nip; and
    a drive coupled to the actuator input, the first pair of index rollers and the second pair of index rollers;
    and wherein upon actuation of the actuator input by a patient, the drive causes rotation of the first and second pairs of index rollers, which in turn, pull a portion of the first and second strips through the first and second nips, respectively.

6. The device of claim 5, wherein the drive comprises a gear, the gear engaging one of the first pair of index rollers and one of the second pair of index rollers, the gear being coupled to the actuator input such each actuation of the actuator input causes a predetermined rotation of the gear.

7. A delivery device, comprising:
    a sachet park including a plurality of unit doses of a medicament enclosed between a first strip and a second strip;

a first roller spaced apart forward from a second roller, the first strip being wrapped around the first roller, the second strip being wrapped around the second roller;

an actuator that, upon actuation by a patient, causes a predetermined rotation of the first roller and second rollers, the predetermined rotation being selected such that repeated actuation of the actuator will cause successive ones of the plurality of the unit doses to be released from the sachet pack; and a mouthpiece positioned relative to the sachet pack, the first roller, and the second roller, to deliver the unit dose of the medicament to an oral cavity of the patient, wherein the actuator includes an actuator input;

a first pair of index rollers defining a first nip therebetween, the first strip passing through the first nip;

a second pair of index rollers defining a second nip therebetween, the second strip passing though the second nip; and a drive coupled to the actuator input, the first pair of index rollers and the second pair of index rollers;

and wherein upon actuation of the actuator input by a patient, the drive causes rotation of the first and second pairs of index rollers, which in turn, pull a portion of the first and second strips through the first and second nips, respectively.

8. The device of claim 7, wherein the drive comprises a gear, the gear engaging one of the first pair of index rollers and one of the second pair of index rollers, the gear being coupled to the actuator input such each actuation of the actuator input causes rotation of the gear in an amount sufficient to cause the predetermined rotation of the first and second rollers.

9. A delivery device, comprising:

a sachet pack including a plurality of unit doses of a medicament enclosed between a first strip and a second strip;

a first member;

a second member;

an actuator, the actuator pulling the first strip against the first member and the second strip against the second member to release a unit dose of the medicament from the a sachet pack; and a mouthpiece positioned relative to the sachet pack, the first member, and the second member, to deliver the unit dose of the medicament to an oral cavity of a patient, wherein the actuator includes an actuator input coupled to a carriage, wherein the carriage is coupled to the first and second strips, and wherein actuation of the actuator input causes a movement of the carriage away from the first and second members.

10. A delivery device, comprising:

a sachet pack including a plurality of unit doses of a medicament enclosed between a first strip and a second strip;

a first member;

a second member;

an actuator, the actuator pulling the first strip against the first member and the second strip against the second member to release a unit dose of the medicament from the a sachet pack; and a mouthpiece positioned relative to the sachet pack, the first member, and the second member, to deliver the unit dose of the medicament to an oral cavity of a patient, wherein the actuator includes an actuator input coupled to a carriage, wherein the carriage is coupled to the first and second strips wherein actuation of the actuator input causes a movement of the carriage from a first position to a second position and then to the first position, the first position being closer to the first and second members than the second position.

11. The device of claim 10, wherein the carriage includes a first draw roller and a second draw roller, the first and second draw rollers being rotationally fixed when the carriage moves from the first position to the second position, the first draw roller rotating to wrap the first strip thereabout when the carriage moves from the second position to the first position, the second draw roller rotating to wrap the second strip thereabout when the carriage moves from the second position to the first position.

12. A delivery device, comprising:

a sachet pack including a plurality of unit doses of a medicament enclosed between a first strip and a second strip;

a first roller spaced apart forward from a second roller, the first strip being wrapped around the first roller, the second strip being wrapped around the second roller;

an actuator, the actuator, upon actuation by a patient, pulling the first strip around the first roller and pulling the second strip around the second roller to release a unit dose of the medicament from the sachet pack; and a mouthpiece positioned relative to the sachet pack, the first roller, and the second roller, to deliver the unit dose of the medicament to an oral cavity of the patient, wherein the actuator includes an actuator input coupled to a carriage, wherein the carriage is coupled to the first and second strips, and wherein actuation of the actuator input causes a movement of the carriage away from the first and second rollers.

13. A delivery device, comprising:

a sachet pack including a plurality of unit doses of a medicament enclosed between a first strip and a second strip;

a first roller spaced apart forward from a second roller, the first strip being wrapped around the first roller, the second strip being wrapped around the second roller;

an actuator, the actuator, upon actuation by a patient, pulling the first strip around the first roller and pulling the second strip around the second roller to release a unit dose of the medicament from the sachet pack; and a mouthpiece positioned relative to the sachet pack, the first roller, and the second roller, to deliver the unit dose of the medicament to an oral cavity of the patient, wherein the actuator includes an actuator input coupled to a carriage, wherein the carriage is coupled to the first and second strips wherein actuation of the actuator input causes a movement of the carriage from a first position to a second position and then to the first position, the first position being closer to the first and second rollers than the second position.

14. The device of claim 13, wherein the carriage includes a first draw roller and a second draw roller, the first and second draw rollers being rotationally fixed when the carriage moves from the first position to the second position, the first draw roller rotating to wrap the first strip thereabout when the carriage moves from the second position to the first position, the second draw roller rotating to wrap the second strip thereabout when the carriage moves from the second position to the first position.

15. A delivery device, comprising:

a sachet pack including a plurality of unit doses of a medicament enclosed between a first strip and a second strip;

a first roller spaced apart forward from a second roller, the first strip being wrapped around the first roller, the second strip being wrapped around the second roller;

an actuator that, upon actuation by a patient, causes a predetermined rotation of the first and second rollers, the predetermined rotation being selected such that repeated actuation of the actuator will cause successive ones of the plurality of the unit doses to be released from the sachet pack;

a mouthpiece positioned relative to the sachet pack, the first roller, and the second roller, to deliver the unit dose of the medicament to an oral cavity of the patient, wherein the actuator includes an actuator input coupled to a carriage, wherein the carriage is coupled to the first and second strips wherein actuation of the actuator input causes a movement of the carriage from a first position to a second position and then to the first position, the first position being closer to the first and second rollers than the second position.

16. The device of claim 15, wherein the carriage includes a first draw roller and a second draw roller, the first and second draw rollers being rotationally fixed when the carriage moves from the first position to the second position, the first draw roller rotating to wrap the first strip thereabout when the carriage moves from the second position to the first position, the second draw roller rotating to wrap the second strip thereabout when the carriage moves from the second position to the first position.

17. A delivery device, comprising:

a sachet pack including a plurality of unit doses of a medicament enclosed between a first strip and a second strip;

a first roller spaced apart forward from and above a second roller, the first strip being wrapped around the first roller, the second strip being wrapped around the second roller;

an actuator, the actuator, upon actuation by a patient, pulling the first strip around the first roller and pulling the second strip around the second roller to release a unit dose of the medicament from the sachet pack; and a mouthpiece surrounding the first and second rollers, the mouthpiece having a top surface, a bottom surface, and a pair of lateral surfaces, the bottom surface having an opening formed therein, the released medicament passing through the opening, wherein the actuator includes an actuator input coupled to a carriage, wherein the carriage is coupled to the first and second strips wherein actuation of the actuator input causes a movement of the carriage from a first position to a second position and then to the first position, the first position being closer to the first and second rollers than the second position.

18. The device of claim 17, wherein the carriage includes a first draw roller and a second draw roller, the first and second draw rollers being rotationally fixed when the carriage moves from the first position to the second position, the first draw roller rotating to wrap the first strip thereabout when the carriage moves from the second position to the first position, the second draw roller rotating to wrap the second strip thereabout when the carriage moves from the second position to the first position.

19. A delivery device, comprising:

a sachet pack including a plurality of unit doses of a medicament enclosed between a first strip and a second strip;

a first member;

a second member;

an actuator, the actuator pulling the first strip against the first member and the second strip against the second member to release a unit dose of the medicament from the a sachet pack; and a mouthpiece positioned relative to the sachet pack, the first member, and the second member, to deliver the unit dose of the medicament to an oral cavity of a patient, wherein the actuator includes a stored energy component;

a stored energy initiator coupled to the stored energy component, wherein the stored energy initiator, upon actuation, stores energy in the stored energy component;

an actuation trigger which, upon actuation, releases the energy from the stored energy component; and a draw component coupled to the stored energy component, the draw component pulling the first strip against the first member and the second strip against the second member when the energy is released from the stored energy component, wherein the draw component comprises a first pair of index rollers defining a first nip therebetween, the first strip passing through the first nip;

a second pair of index rollers defining a second nip therebetween, the second strip passing though the second nip; and a drive coupled to the stored energy component, the first pair of index rollers and the second pair of index rollers;

and wherein upon release of the energy from the stored energy component, the drive causes rotation of the first and second pairs of index rollers, which in turn, pull a portion of the first and second strips through the first and second nips, respectively.

20. The device of claim 19, wherein the drive comprises a first gear, the first gear engaging one of the first pair of index rollers and one of the second pair of index rollers, the first gear being coupled to the actuator input such each actuation of the actuator input causes a predetermined rotation of the gear;

wherein the stored energy component includes a second gear and a torsion element, the second gear engaged with the first gear, the torsion element coupled between the stored energy initiator and the second gear.

21. A delivery device, comprising:

a sachet pack including a plurality of unit doses of a medicament enclosed between a first strip and a second strip;

a first roller spaced apart forward from a second roller, the first strip being wrapped around the first roller, the second strip being wrapped around the second roller;

an actuator, the actuator, upon actuation by a patient, pulling the first strip around the first roller and pulling the second strip around the second roller to release a unit dose of the medicament from the sachet pack;

a mouthpiece positioned relative to the sachet pack, the first roller, and the second roller, to deliver the unit dose of the medicament to an oral cavity of the patient, wherein the actuator includes a stored energy component;

a stored energy initiator coupled to the stored energy component, wherein the stored energy initiator, upon actuation, stores energy in the stored energy component;

an actuation trigger which, upon actuation, releases the energy from the stored energy component; and a draw component coupled to the stored energy component, the draw component pulling the first strip against the first member and the second strip against the second member, wherein the draw component comprises a first pair of index rollers defining a first nip therebetween, the first strip passing through the first nip;

a second pair of index rollers defining a second nip therebetween, the second strip passing though the second nip; and a drive coupled to the stored energy component, the first pair of index rollers and the second pair of index rollers;

and wherein upon release of the energy from the stored energy component, the drive causes rotation of the first and second pairs of index rollers, which in turn, pull a portion of the first and second strips through the first and second nips, respectively.

22. The device of claim 21, wherein the drive comprises a first gear, the first gear engaging one of the first pair of index rollers and one of the second pair of index rollers, the first gear being coupled to the actuator input such each actuation of the actuator input causes a predetermined rotation of the gear;

wherein the stored energy component includes a second gear and a torsion element, the second gear engaged with the first gear, the torsion element coupled between the stored energy initiator and the second gear.

23. A delivery device, comprising:

a sachet pack including a plurality of unit doses of a medicament enclosed between a first strip and a second strip;

a first roller spaced apart forward from a second roller, the first strip being wrapped around the first roller, the second strip being wrapped around the second roller;

an actuator that, upon actuation by a patient, causes a predetermined rotation of the first and second rollers, the predetermined rotation being selected such that repeated actuation of the actuator will cause successive ones of the plurality of the unit doses to be released from the sachet pack;

a mouthpiece positioned relative to the sachet pack, the first roller, and the second roller, to deliver the unit dose of the medicament to an oral cavity of the patient, wherein the actuator includes a stored energy component, and a stored energy initiator coupled to the stored energy component, wherein the stored energy initiator, upon actuation, stores energy in the stored energy component;

an actuation trigger which, upon actuation, releases the energy from the stored energy component; and a draw component coupled to the stored energy component, the draw component pulling the first strip against the first member and the second strip against the second member when the energy is released from the stored energy component, wherein the draw component comprises a first pair of index rollers defining a first nip therebetween, the first strip passing through the first nip;

a second pair of index rollers defining a second nip therebetween, the second strip passing though the second nip; and a drive coupled to the stored energy component, the first pair of index rollers and the second pair of index rollers;

and wherein upon release of the energy from the stored energy component, the drive causes rotation of the first and second pairs of index rollers, which in turn, pull a portion of the first and second strips through the first and second nips, respectively.

24. The device of claim 23, wherein the drive comprises a first gear, the first gear engaging one of the first pair of index rollers and one of the second pair of index rollers, the first gear being coupled to the actuator input such each actuation of the actuator input causes a predetermined rotation of the gear;

wherein the stored energy component includes a second gear and a torsion element, the second gear engaged with the first gear, the torsion element coupled between the stored energy initiator and the second gear.

25. A delivery device, comprising:

a sachet pack including a plurality of unit doses of a medicament enclosed between a first strip and a second strip;

a first roller spaced apart forward from and above a second roller, the first strip being wrapped around the first roller, the second strip being wrapped around the second roller;

an actuator, the actuator, upon actuation by a patient, pulling the first strip around the first roller and pulling the second strip around the second roller to release a unit dose of the medicament from the sachet pack;

a mouthpiece surrounding the first and second rollers, the mouthpiece having a top surface, a bottom surface, and a pair of lateral surfaces, the bottom surface having an opening formed therein, the released medicament passing through the opening, wherein the actuator includes a stored energy component, and a stored energy initiator coupled to the stored energy component, wherein the stored energy initiator, upon actuation, stores energy in the stored energy component;

an actuation trigger which, upon actuation, releases the energy from the stored energy component; and a draw component coupled to the stored energy component, the draw component pulling the first strip against the first member and the second strip against the second member when the energy is released from the stored energy component, wherein the draw component comprises a first pair of index rollers defining a first nip therebetween, the first strip passing through the first nip;

a second pair of index rollers defining a second nip therebetween, the second strip passing though the second nip; and a drive coupled to the stored energy component, the first pair of index rollers and the second pair of index rollers;

and wherein upon release of the energy from the stored energy component, the drive causes rotation of the first and second pairs of index rollers, which in turn, pull a portion of the first and second strips through the first and second nips, respectively.

26. The device of claim 25, wherein the drive comprises a first gear, the first gear engaging one of the first pair of index rollers and one of the second pair of index rollers, the first gear being coupled to the actuator input such each actuation of the actuator input causes a predetermined rotation of the gear;

wherein the stored energy component includes a second gear and a torsion element, the second gear engaged with the first gear, the torsion element coupled between the stored energy initiator and the second gear.

* * * * *